United States Patent
Cho et al.

(10) Patent No.: US 10,809,263 B2
(45) Date of Patent: Oct. 20, 2020

(54) ANTIGENIC COMPOSITION FOR DETECTING AUTO-ANTIBODY WITH SPECIFIC RESPONSE TO EXOSOMAL PROTEIN EIF3A, AND METHOD FOR DIAGNOSING LIVER CANCER USING ANTIGENIC COMPOSITION

(71) Applicants: Korea Research Institute of Bioscience and Biotechnology, Daejeon (KR); ProteomeTech Inc., Seoul (KR)

(72) Inventors: Eun Wie Cho, Daejeon (KR); Chang Kyu Heo, Daejeon (KR); Hai Min Hwang, Daejeon (KR); Jeong Heon Ko, Daejeon (KR); Kook Jin Lim, Seoul (KR); Hye Jung Lee, Seoul (KR)

(73) Assignees: PROTEOMETECH INC., Seoul (KR); KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 86 days.

(21) Appl. No.: 15/743,471

(22) PCT Filed: Jul. 8, 2016

(86) PCT No.: PCT/KR2016/007415
§ 371 (c)(1),
(2) Date: Jan. 10, 2018

(87) PCT Pub. No.: WO2017/010744
PCT Pub. Date: Jan. 19, 2017

(65) Prior Publication Data
US 2019/0204324 A1    Jul. 4, 2019

(30) Foreign Application Priority Data

Jul. 10, 2015    (KR) .................... 10-2015-0098665

(51) Int. Cl.
| | | |
|---|---|---|
| G01N 33/574 | (2006.01) | |
| C07K 16/18 | (2006.01) | |
| A61P 35/00 | (2006.01) | |
| C12N 5/16 | (2006.01) | |
| C07K 16/30 | (2006.01) | |
| G01N 33/58 | (2006.01) | |
| G01N 33/564 | (2006.01) | |
| C07K 14/47 | (2006.01) | |

(52) U.S. Cl.
CPC ........ *G01N 33/57438* (2013.01); *A61P 35/00* (2018.01); *C07K 14/4748* (2013.01); *C07K 16/18* (2013.01); *C07K 16/303* (2013.01); *C12N 5/163* (2013.01); *G01N 33/564* (2013.01); *G01N 33/58* (2013.01); *C07K 2317/14* (2013.01); *C07K 2317/34* (2013.01); *G01N 2800/52* (2013.01)

(58) Field of Classification Search
CPC .......... G01N 33/57438; G01N 33/574; C07K 16/18; C07K 16/303; A61P 35/00
USPC ........................................................ 435/7.23
See application file for complete search history.

(56) References Cited

U.S. PATENT DOCUMENTS

2010/0261209 A1    10/2010  Tseng et al.

FOREIGN PATENT DOCUMENTS

| KR | 2006-0102592 A | 9/2006 |
| KR | 2011-0040624 A | 4/2011 |
| KR | 2012-0134547 A | 12/2012 |
| WO | WO 93/11161 | 6/1993 |
| WO | WO 94/13804 | 6/1994 |
| WO | WO 2015/071669 A2 | 5/2015 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
(Continued)

*Primary Examiner* — Yan Xiao
(74) *Attorney, Agent, or Firm* — John P. White; Gary J. Gershik; Cooper & Dunham LLP

(57) ABSTRACT

Provided are an autoantibody specifically binding to an exosomal protein EIF3A (Eukaryotic translation initiation factor 3 subunit A) or a fragment including an antigen-binding site (paratope) thereof, a hybridoma cell line producing the autoantibody, a polypeptide having an amino acid sequence of an antigenic determinant (epitope) specifically binding to the autoantibody, a composition for diagnosing liver cancer including an agent measuring an expression level of the autoantibody or the fragment including the antigen-binding site thereof, a kit for diagnosing liver cancer including the composition, and a method of providing information for diagnosis of liver cancer by using the composition. Further, provided is a method of screening for a therapeutic agent for liver cancer by using an expression level of the autoantibody. When anti-EIF3A autoantibody of the present invention is used as a diagnostic marker for liver cancer, the incidence of liver cancer may be diagnosed at a high level only by using non-invasive biological samples. Furthermore, liver cancer may be easily diagnosed by using only the amino acid sequence identified in the present invention, leading to the effective development of diagnostic products such as a diagnostic kit for liver cancer.

11 Claims, 17 Drawing Sheets

Specification includes a Sequence Listing.

(56) References Cited

OTHER PUBLICATIONS

Hershey, "The role of eIF3 and its individual subunits in cancer" Biochimica et Biophysica Acta, (Nov. 1, 2014), vol. 1849, pp. 792-800.
Spilka, et al., "Overexpression of eIF3a in squamous cell carcinoma of the oral cavity and its putative relation to chemotherapy response", Journal of Oncology, (2012), vol. 2012, Article ID 901956.
Shen, et al., "The prognostic value of altered eIF3a and its association with p27 in non-small cell lung cancers" Plos One, (2014), vol. 9, Issue 4, Article No. ep6008.
Michal Grzmil, et al., "Translation Regulation as a Therapeutic Target in Cancer", Cancer Research, (2012), vol. 72(16), pp. 3891-3900.
Korean Ministry of Education, Science and Technology, Research Project for Senior Researchers final report, (2011).
International Search Report dated Nov. 1, 2016 in connection with PCT International Application No. PCT/KR2016/007415.

\* cited by examiner

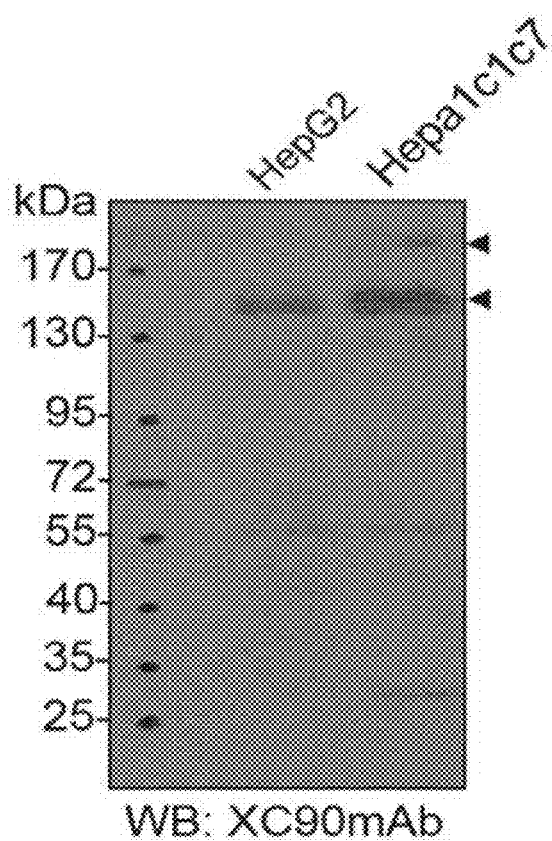

| Gene Symbol | Accession Number | Molecular Mass (Da) | Queries Matched | Mascot Score |
|---|---|---|---|---|
| EIF3A eukaryotic translation initiation factor3A, subunit A | IPI00029012 | 166468 | 4 | 156 |

FIG. 4d

| Phage antigen | Epitope sequence | | | | | | *OD$_{450nm}$ |
|---|---|---|---|---|---|---|---|
| XC90p2 | P | V | R | S | G | F | P | 2.77 |
| XC90p9 | P | A | R | S | G | Y | P | 2.15 |
| XC90p7 | P | A | R | T | S | W | P | 2.45 |
| XC90p8 | P | A | R | T | G | F | Q | 2.64 |
| XC90p6 | P | A | R | H | S | G | F | 2.70 |
| XC90p4 | P | S | R | H | S | G | W | 2.77 |
| XC90p5 | P | S | R | H | S | G | Y | 2.01 |
| XC90p10 | F | P | F | P | S | S | L | 1.61 |
| XC90p1 | F | P | F | P | S | S | L | 1.38 |
| XC90p3 | L | P | W | P | S | S | L | 0.69 |

XC90VL

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|
| GAY | ATT | GTG | ATC | ACC | CAR | WCT | MCA | GCA | ATC | ATG | TCT | GCA | TCT | CCA | GGG | GAG | AAG | GTC | ACC | ATA | TCC | TGC | AGT |
| D | I | V | I | T | Q | X | T | A | I | M | S | A | S | P | G | E | K | V | T | I | S | C | S |
|   |   |   |   |   |   |   |   |   |   |   |   |   |   |   |   |   |   |   |   | CDR-L1 |   |   |   |

| 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|---|---|---|---|---|---|---|
| GCC | AGT | TCA | AGT | GTA | AGT | TAC | ATG | TGG | TAC | CAG | AAG | CCA | GGA | TCC | TCC | CCC | AAA | CCC | TGG | ATT | TAT |
| A | S | S | S | V | S | Y | M | Y | W | Y | Q | Q | K | P | G | S | S | P | K | P | W | I | Y |
|   | CDR-L1 |   |   |   |   |   |   |   |   |   |   |   |   |   |   |   |   |   |   |   |   |   |   |

| 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|---|---|---|---|---|
| CGC | ACA | TCC | AAC | CTG | GCT | TCT | GGA | GTC | CCT | GCT | CGC | TTC | AGT | GGC | AGT | GGG | TCT | GGG | ACC | TCT | TAC | TCT | CTC |
| R | T | S | N | L | A | S | G | V | P | A | R | F | S | G | S | G | S | G | T | S | Y | S | L |
|   | CDR-L2 |   |   |   |   |   |   |   |   |   |   |   |   |   |   |   |   |   |   |   |   |   |   |

| 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|---|---|---|---|---|---|---|
| ACA | ATC | AGC | AGC | ATG | GAG | GCT | GAA | GAT | GCT | GCC | ACT | TAT | TAC | TGC | CAG | CAG | TAT | CAT | AGT | TAC | CCA | CCG | ACG |
| T | I | S | S | M | E | A | E | D | A | A | T | Y | Y | C | Q | Q | Y | H | S | Y | P | P | T |
|   |   |   |   |   |   |   |   |   |   |   |   |   |   | CDR-L3 |   |   |   |   |   |   |   |   |   |

| 97 | 98 | 99 | 100 | 101 | 102 | 103 | 104 | 105 | 106 | 107 | 108 | 109 | 110 | 111 | 112 | 113 | 114 | 115 |
|---|---|---|---|---|---|---|---|---|---|---|---|---|---|---|---|---|---|---|
| TTC | GGT | GGA | GGC | ACC | AAG | CTG | GAA | ATC | AAA | CGG | GCT | GAT | GCT | GCA | CCA | ACT | GTA | TCC (SEQ ID NO: 31) |
| F | G | G | G | T | K | L | E | I | K | R | A | D | A | A | P | T | V | S (SEQ ID NO: 23) |

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|----|----|----|----|----|----|----|----|----|----|----|----|----|----|----|
| SAR | GTM | AAG | CTG | SAG | GAG | TCT | GGG | GCT | GAG | CTT | GTG | ATG | CCT | GGG | GCT | TCA | GTG | AAG | CTG | TCC | TGC | AAG | GCT |
| X | V | K | L | X | E | S | G | A | E | L | V | M | P | G | A | S | V | K | L | S | C | K | A |

CDR-H1

| 25 | 26 | 27 | 28 | 29 | 30 | 31 | 32 | 33 | 34 | 35 | 36 | 37 | 38 | 39 | 40 | 41 | 42 | 43 | 44 | 45 | 46 | 47 | 48 |
|----|----|----|----|----|----|----|----|----|----|----|----|----|----|----|----|----|----|----|----|----|----|----|----|
| TCT | GGC | TAC | ACC | TTC | ACC | AGC | TAC | TGG | ATA | CAC | TGG | GTG | AAA | CAG | AGG | CCT | GGA | CAA | GGC | CTT | GAG | TGG | ATC |
| S | G | Y | T | F | T | S | Y | W | I | H | W | V | K | Q | R | P | G | Q | G | L | E | W | I |

CDR-H2

| 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 |
|----|----|----|----|----|----|----|----|----|----|----|----|----|----|----|----|----|----|----|----|----|----|----|----|
| GGA | GAG | ATT | GAT | CCT | TCT | GAT | AGT | TAT | ACT | AAC | TAC | AAT | CAA | AAG | TTC | AAG | GGC | AAG | TCC | ACA | TTG | ACT | GTA |
| G | E | I | D | P | S | D | S | Y | T | N | Y | N | Q | K | F | K | G | K | S | T | L | T | V |

| 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 |
|----|----|----|----|----|----|----|----|----|----|----|----|----|----|----|----|----|----|----|----|----|----|----|----|
| GAC | AAA | TCC | TCC | AAC | ACA | GCC | TAC | ATG | CAG | CTC | AGC | AGC | CTG | ACA | TCT | GAG | GAC | TCT | GCG | GTC | TAT | TAC | TGT |
| D | K | S | S | N | T | A | Y | M | Q | L | S | S | L | T | S | E | D | S | A | V | Y | Y | C |

CDR-H3

| 97 | 98 | 99 | 100 | 101 | 102 | 103 | 104 | 105 | 106 | 107 | 108 | 109 | 110 | 111 | 112 | 113 | 114 | 115 | 116 | 117 | 118 | 119 | 120 |
|----|----|----|-----|-----|-----|-----|-----|-----|-----|-----|-----|-----|-----|-----|-----|-----|-----|-----|-----|-----|-----|-----|-----|
| GCA | AAA | GGC | TCT | TAT | GCC | CCT | TTT | GCT | TAC | TGG | GGC | CAA | GGG | ACT | CTG | GTC | ACT | GTC | TCT | GCA | GAG | AGT | CAG |
| A | K | G | S | Y | A | P | F | A | Y | W | G | Q | G | T | L | V | T | V | S | A | E | S | Q |

| 121 | 122 | 123 | 124 | 125 |
|-----|-----|-----|-----|-----|
| TCC | TTC | CCA | AAT | GTC |
| S | F | P | N | V |

(SEQ ID NO: 30)
(SEQ ID NO: 22)

ANTIGENIC COMPOSITION FOR DETECTING AUTO-ANTIBODY WITH SPECIFIC RESPONSE TO EXOSOMAL PROTEIN EIF3A, AND METHOD FOR DIAGNOSING LIVER CANCER USING ANTIGENIC COMPOSITION

CROSS-REFERENCE TO RELATED APPLICATIONS

This application is a § 371 national stage of PCT International Application No. PCT/KR2016/007415, filed Jul. 8, 2016, claiming priority of Korean Patent Application No. KR 10-2015-0098665, filed Jul. 10, 2015, the contents of each of which are hereby incorporated by reference into the application.

REFERENCE TO A SEQUENCE LISTING

This application incorporates by reference nucleotide and/or amino acid sequences which are present in the file named "200206_90283_Substitute_Sequence_Listing_BI.txt", which is 9.43 kilobytes in size, and which was created Feb. 5, 2020 in the IBM-PC machine format, having an operating system compatibility with MS-Windows, which is contained in the text file filed Feb. 6, 2020 as part of this application.

BACKGROUND OF THE INVENTION

1. Field of the Invention

The present invention relates to an antigenic composition for detecting an autoantibody specific to an exosomal protein EIF3A (eukaryotic translation initiation factor 3 subunit A) and a method of diagnosing liver cancer by using the same. More particularly, the present invention relates to an autoantibody specifically binding to an exosomal protein EIF3A which is induced in the human body or a fragment including an antigen-binding site (paratope) thereof, a hybridoma cell line producing the autoantibody, a polypeptide having an amino acid sequence of an antigenic determinant (epitope) specifically binding to the autoantibody, a composition for diagnosing liver cancer including an agent measuring an expression level of the autoantibody or the fragment including the antigen-binding site thereof, a kit for diagnosing liver cancer including the composition, a method of diagnosing liver cancer by using the composition, and a method of screening for a therapeutic agent for liver cancer by using the expression level of the autoantibody.

2. Description of the Related Art

For diagnosis of cancer, ex-vivo diagnostics of tumor markers is currently used to detect tumor biomarkers in the blood through molecular biological or biochemical studies, together with endoscopic examination, diagnostic imaging, nuclear medicine examination, etc.

Effective tumor markers for ex-vivo diagnostics should confirm the diagnosis of cancer only by a simple blood test and should determine its progression. Most of the tumor markers currently used in clinical practice are CA125, CEA, and PSA which are antigens specifically expressed and secreted in cancer cells. Their serum concentrations are measured by sandwich ELISA. However, the above-mentioned antigens have low sensitivity and specificity for cancer diagnosis, and thus they have been used only as an auxiliary means of cancer diagnosis.

Immune system generally induces a humoral immune response or a cellular immune response against foreign antigens recognized as non-self. However, even when a substance is expressed in the body, it may act as a self-antigen to induce antibody production, in the case where its expression site is different from a normal site, and thus it is secreted out of cells, it exhibits a deformed shape, or its characteristics are different from those of a normal individual. It has been reported that during cancer development, autoantibodies against tumor-associated antigens (TAAs) are produced, accompanied by abnormal cancer cell growth. In addition, autoantibodies induced by the tumor-associated antigens are also found at an early stage of tumorigenesis, and therefore, they are suggested as biomarkers suitable for early diagnosis.

Furthermore, a variety of autoantibodies induced during tumorigenesis are reported in many different kinds of cancer. During development of liver cancer, MDM2 (E3 ubiquitin-protein ligase) which is a negative regulator of p53 tumor suppressor gene and NPM1 (Nucleophosminl) which is a nuclear protein having various functions induce autoantibodies. MUC-1 induces a high level of MUC-1-specific autoantibody due to the lack of sugar chains exposed to cell surface in breast cancer, colon cancer, and lung cancer. In head and neck squamous cell carcinoma, 53% to 93% of a mutant form of p53 protein is overexpressed and abnormally accumulated in cells to induce production of autoantibodies against p53. Also, SOX B1, B2 autoantibodies are found in 43% of small cell lung cancer patients. In the case of diagnosis of nasopharyngeal carcinoma by using EBV autoantibody, the specificity and sensitivity exceed 90%.

It was also an important issue that due to extracellular secretion by post-translational modification or extracellular release of intracellular proteins by necrosis of a tumor site, new epitopes stimulate the immune system to induce antibodies. However, it was recently confirmed that cancer cells utilize membrane vesicles, such as exosome, as an extracellular release system of cellular materials, and therefore, it is expected that stimulation of the immune system by the membrane vesicles may also provide intracellular proteins capable of inducing autoantibodies.

Detection of autoantibodies is advantageous in that a relatively stable diagnostic method may be constructed, as compared with detection of blood protein antigens, and detection is also possible even at the early stage. The detection method is easy to construct as long as a target antigen is secured. Thus, it was confirmed that a multiple detection method is easily constructed and the diagnostic effect is improved when cancer diagnosis is tried by multiple detection of autoantibodies.

Representatively, it was reported that when autoantibodies are detected by using 22 phage-peptide autoimmune antigens selected from phage-display libraries expressing proteins derived from prostate cancer, prostate cancer may be detected with 81.6% sensitivity and 88.2% specificity, suggesting that the diagnostic effect is higher than that of a known marker PSA. When ASB-9, SERAC1, and RELT antigen-reactive autoantibodies are detected at the same time, breast cancer may be detected with 100% specificity and 80% sensitivity. Further, when PIM1, MAPKAPK3, and ACVR2B antigen-reactive autoantibodies are used, colon cancer may be diagnosed with 74% specificity and 83% sensitivity. Recently, it was reported that a Luminex technique of detecting 7 autoantibody biomarkers at the same time may be used to diagnose lung cancer with accuracy of 80% or more.

Based on these results, cancer diagnostic methods by detection of autoantibodies are commercialized and marketed. Oncimmune Ltd. in the UK has constructed an autoantibody multiplex detection method that is suitable for early diagnosis of lung cancer using 7 autoantigens. The product has been marketed as "EarlyCDT-Lung" since 2012, and its range of applications is now expanding to the US market. Therefore, it has been confirmed that cancer diagnosis by multiplex detection of cancer-derived autoantibodies is efficient, and thus it has been suggested that identification of autoantibodies with high specificity and sensitivity is important.

Acquisition of antibody-specific antigens is essential for the detection of cancer-associated autoantibodies in serum. As the most basic method to achieve this purpose, antibody-specific antigen proteins are obtained from cancer cells, and analyzed by proteomics, and then the corresponding antigens are prepared as recombinant proteins, which are then used for the detection of antibodies. Proteomic approaches, such as serological proteome analysis (SERPA) and multiple affinity protein profiling (MAPPING), may be used to identify autoantibody-specific antigens. In addition, a protein chip is prepared by dividing a cancer cell lysate into several thousand fractions, and reactivity of patient's blood in the protein chip may be examined to identify autoantibodies.

As another method, antibody-reactive epitopes are first obtained, and then a protein antigen including the analyzed epitope protein sequence may be identified. Screening of cDNA expression phage libraries or linear peptide libraries for epitope analysis is a method generally used for characterization of antibodies. Linear peptide sequences screened to identify autoantibody antigens may be used to infer antigen proteins, and phages expressing peptides may be directly used to detect antibodies, and therefore, the peptides may be used in the preparation of antigen arrays for autoantibody detection.

Currently, many studies have been conducted to discover autoantibodies associated with cancer diagnosis, such as a method of diagnosing liver diseases by measuring expression levels of autoantibodies specifically binding to various derivative peptides, a method of diagnosing liver cancer by measuring expression levels of autoantibodies specifically binding to ATIC (5-aminoimidazole-4-carboxamide ribonucleotide formyltransferase/IMP cyclohydrolase) protein, etc. For example, US Patent Publication No. 2010-0261209 discloses a technology of using various derivative peptides or autoantibodies specifically binding to the peptides as biomarkers for the detection of liver diseases. Korean Patent Publication No. 2012-0134547 discloses a composition for diagnosing liver cancer, including an agent measuring an expression level of an autoantibody specifically binding to ATIC(5-aminoimidazole-4-carboxamide ribonucleotide formyltransferase/IMP cyclohydrolase) or a fragment including an antigen-binding site thereof.

Since the above diagnostic methods of using autoantibodies have an advantage of easy configuration, as compared with antigen detection methods, and the possibility of early diagnosis has been suggested, attention has been focused on related researches for the last 10 years. However, some problems that arise during processes of identifying cancer-associated autoantibodies and acquiring antigens are obstacles to obtaining useful results.

A first problem is acquisition of autoantibodies to be analyzed. To acquire cancer-associated autoantibodies, patients' sera are used. However, since it is difficult to continuously obtain patients' sera, there is a disadvantage that a sufficient amount thereof cannot be used for characterization. A second problem is that it is difficult to obtain recombinant proteins sufficiently reflecting the structure of the antibody-specific epitope even though antigen proteins are identified. When antibody-specific epitopes recognize sequence characteristics, recombinant proteins with an incomplete high-order structure or antigens derived from linear peptide libraries may be used for antibody detection. However, in the case of antibodies recognizing high order structures, there is a difficulty in acquiring antigens for detection. Considering that antibodies against in vivo antigens commonly induce structure-recognizing antibodies, there are obvious limitations in the studies on the use of autoantibodies, which have been conducted so far.

The present inventors have made many efforts to identify autoantibodies for the diagnosis of liver cancer, and as a result, they found that an autoantibody specifically binding to EIF3A protein may be used as an autoantibody for the diagnosis of liver cancer, thereby completing the present invention.

SUMMARY OF THE INVENTION

An object of the present invention is to provide an autoantibody specifically binding to EIF3A (eukaryotic translation initiation factor 3 subunit A) protein or a fragment including an antigen-binding site thereof.

Another object of the present invention is to provide a hybridoma cell line producing the autoantibody.

Still another object of the present invention is to provide a polypeptide having an amino acid sequence of an antigenic determinant (epitope) specifically binding to the autoantibody.

Still another object of the present invention is to provide a composition for diagnosing liver cancer including an agent measuring an expression level of the autoantibody or the fragment including the antigen-binding site thereof.

Still another object of the present invention is to provide a kit for diagnosing liver cancer including the composition.

Still another object of the present invention is to provide a method of diagnosing liver cancer by using the composition.

Still another object of the present invention is to provide a method of screening for a therapeutic agent for liver cancer by using the composition.

BRIEF DESCRIPTION OF THE DRAWINGS

FIG. 1C is a photograph showing results of Western blot analysis for examining XC90 autoantibody-specific antigen protein;

FIG. 4 is a schematic illustration, graph, and table showing results of selecting XC90 antibody-specific antigen expressing phages by screening phage-display cyclic $CX_7C$-peptide libraries with XC90 antibody;

FIG. 4D is a table showing sequences of epitopes expressed from XC90 antibody-specific antigen expressing phages;

FIG. 8 is a table showing the result of analyzing light chain variable region ($V_L$) of the obtained XC90 antibody as a complementarity determining region (CDR) sequence of XC90 autoantibody (SEQ ID NOS: 31 and 23); and FIG. 9 is a table showing the result of analyzing complementarity determining region (CDR) of heavy chain variable region ($V_H$) of the obtained XC90 antibody as a complementarity determining region (CDR) sequence of XC90 autoantibody (SEQ ID NOS: 30 and 22).

DETAILED DESCRIPTION OF THE PREFERRED EMBODIMENTS

Figure 1A:
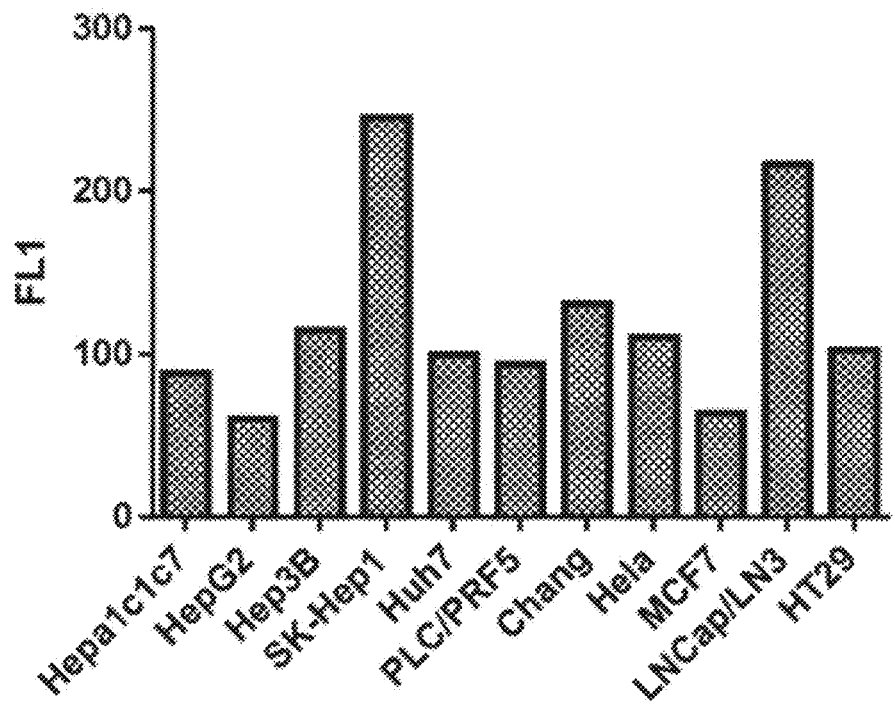
FIG. 1A is a graph showing results of examining reactivity of XC90 antibody against various cancer cells by flow cytometry.

In an aspect to achieve the above objects, the present invention provides an autoantibody specifically binding to EIF3A (eukaryotic translation initiation factor 3 subunit A) protein or a fragment including an antigen-binding site thereof.

As used herein, the term "EIF3A (eukaryotic translation initiation factor 3 subunit A)" refers to a protein constituting a eukaryotic translation initiation factor 3(eIF-3) complex, which is required for several steps in the initiation of protein synthesis. A specific nucleotide sequence of a gene encoding the EIF3A protein and protein information are known in NCBI (GenBank: Accession NM_003750.2, NP_003741.1, etc.).

As used herein, the term "autoantibody" refers to an antibody specifically reactive to an individual's own body component, and is also called self-antibody. In general, since a subject does not induce immune responses against its own substances, it does not produce antibodies. However, in a particular case, the subject may also produce antibodies against its own substances, and these antibodies are called autoantibodies. When autoantibodies are produced, they may cause various diseases, for example, autoimmune diseases such as systemic lupus erythematosus and rheumatoid arthritis.

With respect to the objects of the present invention, the autoantibodies may be specifically, but are not limited to, antibodies against tumor-associated antigens (TAA) accompanied by abnormal cancer cell growth, unlike the above case.

In the present invention, an antigen-binding site of an autoantibody specifically binding to EIF3A of which expression level is increased in liver cancer tissues was identified, and the corresponding antibody was designated as XC90 antibody (hereinafter, referred to as 'anti-EIF3A antibody', 'XC90 antibody', 'XC90 autoantibody', or 'autoantibody XC90'). Further, to characterize the autoantibody, the present inventors analyzed a nucleotide sequence of the autoantibody of the present invention. As a result, it was found that the autoantibody of the present invention is an autoantibody including a heavy chain variable region of SEQ ID NO: 22 and a light chain variable region of SEQ ID NO: 23.

In general, one antibody molecule has two heavy chains and two light chains, each heavy chain and each light chain include a variable region at the N-terminus thereof. Each variable region consists of three complementarity determining regions (CDRs) and four framework regions (FRs). The complementarity determining regions determine antigen-binding specificity of the antibody, and exists as a relatively short peptide sequence maintained by the framework regions of the variable region.

For example, the autoantibody of the present invention may include an autoantibody consisting of heavy chain CDR1 represented by an amino acid sequence of SEQ ID NO: 24; heavy chain CDR2 represented by an amino acid sequence of SEQ ID NO: 25; and heavy chain CDR3 represented by an amino acid sequence of SEQ ID NO: 26 as a part of a heavy chain variable region, or a fragment including an antigen-binding site thereof. The autoantibody of the present invention may be an autoantibody including all of the sequences of CDR1, CDR2, and CDR3, or a fragment thereof. Further, the autoantibody of the present invention may include an autoantibody consisting of light chain CDR1 represented by an amino acid sequence of SEQ ID NO: 27; light chain CDR2 represented by an amino acid sequence of SEQ ID NO: 28; and light chain CDR3 represented by an amino acid sequence of SEQ ID NO: 29 as a part of a light chain variable region, or a fragment including an antigen-binding site thereof.

For another example, the autoantibody of the present invention may be an autoantibody consisting of the amino acid sequence of SEQ ID NO: 22 as the sequence of the heavy chain variable region, or a fragment including an antigen-binding site thereof, and the autoantibody of the present invention may be an autoantibody consisting of the amino acid sequence of SEQ ID NO: 23 as the sequence of the light chain variable region, or a fragment including an antigen-binding site thereof. Further, the heavy chain and the light chain may be used individually or in combination according to the purpose, and it is possible for a person skilled in the art to freely combine a number of CDR sequences and light chains and heavy chains by a common genetic engineering method according to the purpose. Furthermore, it is apparent that the nucleotide sequences encoding the sequences are also included in the present invention.

There have been no reports about formation of autoantibodies in liver cancer by EIF3A of the present invention. Especially, the present inventors demonstrated for the first time that autoantibodies against EIF3A are significantly increased in a subject with liver cancer, leading to identification of a peptidomimetic sequence represented by an amino acid sequence similar to that of the antigenic determinant (epitope) of EIF3A.

The autoantibody of the present invention includes a polynucleotide encoding two full-length heavy chains or a fragment having an immunological activity of the antibody molecule to achieve antibody-antigen binding. Further, the autoantibody of the present invention includes a polynucleotide encoding two full-length light chains or a fragment having an immunological activity of the antibody molecule to achieve antibody-antigen binding. The fragment having the immunological activity of the antibody molecule indicates a fragment retaining antigen-binding capacity, and examples of the antibody fragment include (i) the Fab fragment consisting of a light chain variable region ($V_L$), a heavy chain variable region ($V_H$), a light chain constant region ($C_L$) and a heavy chain constant region 1 (CH1); (ii) the Fd fragment consisting of the $V_H$ and CH1 domains; (iii) the Fv fragment consisting of the $V_L$ and $V_H$ domains of a monoclonal antibody; (iv) the dAb fragment (Ward E S et al., Nature 341:544-546 (1989)) which consists of a $V_H$ domain; (v) isolated CDR regions; (vi) F(ab')2 fragments, a bivalent fragment including two linked Fab fragments; (vii) single chain Fv molecules (scFv), in which a $V_H$ domain and a $V_L$ domain are linked by a peptide linker which allows the two domains to be connected to form an antigen binding site; (viii) bispecific single chain Fv dimers (PCT/US92/09965) and (ix) "diabodies", multivalent or multispecific fragments constructed by gene fusion (WO94/13804), but are not limited thereto.

Specifically, the autoantibody of the present invention or the fragment including the antigen-binding site thereof may be an autoantibody or a fragment including an antigen-binding site thereof produced by a hybridoma cell line deposited under Accession No. KCTC 12590BP. More specifically, the autoantibody of the present invention or the fragment including the antigen-binding site thereof may be an autoantibody or a fragment including an antigen-binding site thereof recognizing an amino acid sequence of FPFPSSL (Phe-Pro-Phe-Pro-Ser-Ser-Leu) represented by SEQ ID NO: 1, PVRSGFP (Pro-Val-Arg-Ser-Gly-Phe-Pro) represented by SEQ ID NO: 2, LPWPSSL (Leu-Pro-Trp-Pro-Ser-Ser-Leu) represented by SEQ ID NO: 3, PSRHSGW (Pro-Ser-Arg-His-Ser-Gly-Trp) represented by SEQ ID NO: 4, PSRHSGY (Pro-Ser-Arg-His-Ser-Gly-Tyr) represented by SEQ ID NO: 5, PARHSGF (Pro-Ala-Arg-His-Ser-Gly-Phe) represented by SEQ ID NO: 6, PARTSWP (Pro-Ala-Arg-Thr-Ser-Trp-Pro) represented by SEQ ID NO: 7, PPRTGFQ (Pro-Pro-Arg-Thr-Gly-Phe-Gln) represented by SEQ ID NO: 8, or PARSGYP (Pro-Ala-Arg-Ser-Tyr-Pro) represented by SEQ ID NO: 9. Much more specifically, the autoantibody of the present invention or the fragment including the antigen-binding site thereof may be an autoantibody or a fragment including an antigen-binding site thereof recognizing the amino acid sequence of PVRSGFP represented by SEQ ID NO: 2. F represents phenylalanine (Phe), P represents proline (Pro), S represents serine (Ser), L represents leucine (Leu), V represents valine (Val), represents arginine (Arg), G represents glycine (Gly), W represents tryptophan (Trp), H represents histidine (His), A represents alanine (Ala), Y represents tyrosine (Tyr), and Q represents glutamine (Gln) among 20 essential amino acids.

In order to identify a sequence of an antigenic determinant, i.e., epitope binding to the autoantibody of the present invention, the present inventors utilized phage-display cyclic peptide library system forming a cyclic structure by 7 amino acids. Specifically, phages specifically binding to anti-EIF3A autoantibody were selected. From the selected phages, phage groups showing high reactivity to anti-EIF3A autoantibody of the present invention were only purified and employed as coating antigens, and then reactivity of immune antibodies binding to the antigens was examined to analyze their amino acid sequence.

In another aspect, the present invention provides a hybridoma cell line producing the autoantibody.

As used herein, the term "hybridoma" refers to a cell prepared by artificial fusion of two different types of cells, and a fused cell of two or more homogenous cells or heterogeneous cells prepared by using a substance inducing cell fusion such as polyethylene glycol or a type of virus. A hybridoma is to integrate different functions of different cells into one cell, and is represented by lymphocytes. In particular, a hybrid cell, which is prepared by the fusion of myeloma cells and B cell which is a precursor cell responsible for producing antibodies among lymphocytes in the spleen or lymph node, produces monoclonal antibodies, and thus it is widely used in researches or clinical trials. In addition, hybridomas of lymphokines (physiologically active substance)-producing T cells and their tumor cells are also practically used. The hybridoma producing the autoantibody of the present invention may be suitably prepared by modification of the cells known in the art by those skilled in the art.

In one embodiment of the present invention, a mouse myeloma cell Sp2/0 and B cell were fused and cultured, and then only B cell hybridomas producing cancer cell-reactive antibodies were selected, and deposited at Biological Resource Center, Korea Research Institute of Bioscience and Biotechnology under the Accession No. KCTC 12590BP on May 12, 2014. Specifically, the hybridoma cell line may be a cell line deposited under Accession No. KCTC 12590BP.

In still another aspect, the present invention provides a polypeptide having the amino acid sequence of FPFPSSL represented by SEQ ID NO: 1, PVRSGFP represented by SEQ ID NO: 2, LPWPSSL represented by SEQ ID NO: 3, PSRHSGW represented by SEQ ID NO: 4, PSRHSGY represented by SEQ ID NO: 5, PARHSGF represented by SEQ ID NO: 6, PARTSWP represented by SEQ ID NO: 7, PPRTGFQ represented by SEQ ID NO: 8, or PARSGYP represented by SEQ ID NO: 9, which is an epitope specifically binding to the autoantibody.

Specifically, polypeptides consisting of the seven amino acids are prepared to include additional cysteines (Cys; C) at both ends in the form of $CX_7C$, and thus they are able to form a stable cyclic structure. Such polypeptides may be used as an epitope-mimetic polypeptide detecting the autoantibody of the present invention. In a specific embodiment of the present invention, a phage expressing cyclic peptide library (Ph.D.-C7C Phage Display Peptide Library kit; New England Biolabs), where 7 amino acids having cysteines at both ends form a cyclic structure, was used to identify PVRSGFP represented by SEQ ID NO: 2 showing high reactivity to XC90mAb autoantibody from random sequences.

In still another aspect, the present invention provides a composition for diagnosing liver cancer, comprising an agent measuring an expression level of the autoantibody or the fragment comprising the antigen-binding site thereof.

As used herein, the term "diagnosis" refers to evaluation of the presence or properties of pathological states. With respect to the objects of the present invention, diagnosis includes not only the determination of the incidence of liver cancer but also the prediction of the outcomes of the treatment, including recurrence, metastatic spread, and drug reactivity and resistance. Specifically, the autoantibody specifically binding to EIF3A of the present invention is used to determine the expression level of EIF3A in a sample isolated from an individual suspected of having liver cancer, thereby predicting the prognosis of the individual as well as diagnosing the incidence of liver cancer. More specifically, the autoantibody may be an antibody specifically binding to the amino acid sequence of FPFPSSL represented by SEQ ID NO: 1, PVRSGFP represented by SEQ ID NO: 2, LPWPSSL represented by SEQ ID NO: 3, PSRHSGW represented by SEQ ID NO: 4, PSRHSGY represented by SEQ ID NO: 5, PARHSGF represented by SEQ ID NO: 6, PARTSWP represented by SEQ ID NO: 7, PPRTGFQ represented by SEQ ID NO: 8, or PARSGYP represented by SEQ ID NO: 9. Much more specifically, the autoantibody may be an antibody specifically binding to the amino acid sequence of PVRSGFP represented by SEQ ID NO: 2. Still much more specifically, the autoantibody may be an antibody specifically binding to the amino acid sequence of PVRSGFP represented by SEQ ID NO: 2, but is not limited thereto.

As used herein, the term "sample of an individual" includes a sample such as a tissue, a cell, whole blood, serum, plasma, saliva, sputum, cerebrospinal fluid, or urine that shows a difference in the expression levels of EIF3A, but is not limited thereto.

As used herein, the term "diagnostic marker, marker used for diagnosis, marker for diagnosis, or diagnosis marker", is intended to indicate a substance capable of diagnosing cancer by distinguishing cancer cells from normal cells. Specifically, the diagnostic marker of the present invention may be an autoantibody specifically binding to EIF3A for the diagnosis of liver cancer.

Figure 7:
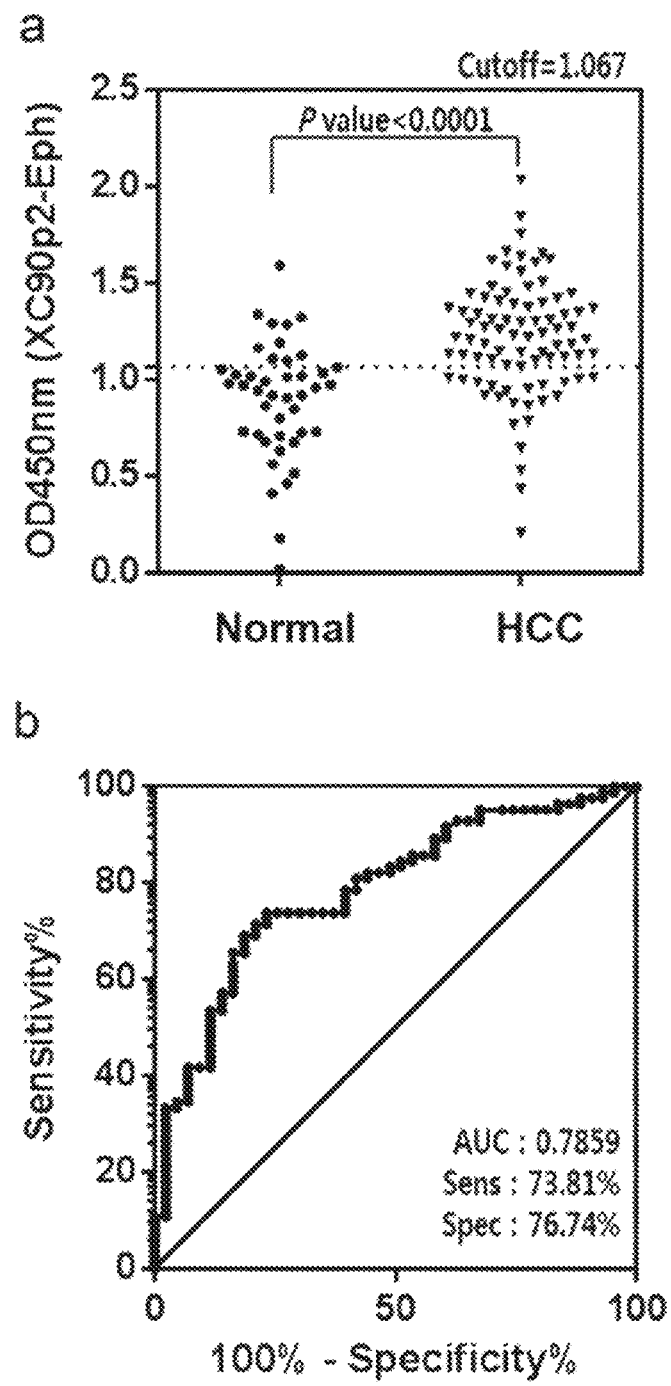
FIG. 7 is a graph showing the result of diagnosing liver cancer by using XC90p2 epitope-expressing recombinant protein, in which A is a graph showing the result of diagnosing a control group (normal) and a liver cancer patient (HCC), and B is a graph showing diagnostic specificity by analyzing the diagnostic result.

As used herein, the term "liver cancer" refers to a malignant tumor derived from hepatic cells accounting for most of the liver, and encompasses all kinds of malignant tumors that begin within the liver (e.g., intrahepatic cholangiocarcinoma) and metastatic hepatocellular carcinoma that spread to the liver from other sites. The prognosis of liver cancer depends on the number and size of tumors, the extent of the vascular invasion, etc. The main cause of death in patients with liver cancer is not liver cancer itself but hepatic failure due to liver cancer progression. Accordingly, the present inventors confirmed that the autoantibody of the present invention may be used to diagnose the incidence of liver cancer in a subject with high specificity (FIG. 7).

The known methods which detect proteins overexpressed in cancer are not suitable for diagnosing cancer because of reduced half-life of tumor-specific protein released into the blood. Thus, it is problematic for use as a diagnostic marker for cancer. The EIF3A-specific autoantibody of the present invention has a long half-life to show high detection sensitivity, and samples like blood may be also simply collected from patients by a non-invasive method. Thus, the autoantibody of the present invention is suitably used as a diagnostic marker for cancer.

As used herein, the term "agent capable of measuring an expression level of the autoantibody specifically binding to EIF3A protein or the fragment including the antigen-binding site thereof" means a molecule that is used for the detection of the marker by measuring the expression level of anti-EIF3A autoantibody, which is a marker overexpressed in the whole blood, serum, plasma, lymphatic fluid and interstitial fluid of individuals with liver cancer or suspected of having liver cancer. Specifically, it may be a polypeptide specifically binding to the autoantibody. The polypeptide specifically binding to the autoantibody may be a polypeptide having the amino acid sequence of FPFPSSL represented by SEQ ID NO: 1, PVRSGFP represented by SEQ ID NO: 2, LPWPSSL represented by SEQ ID NO: 3, PSRHSGW represented by SEQ ID NO: 4, PSRHSGY represented by SEQ ID NO: 5, PARHSGF represented by SEQ ID NO: 6, PARTSWP represented by SEQ ID NO: 7, PPRTGFQ represented by SEQ ID NO: 8, or PARSGYP represented by SEQ ID NO: 9. The polypeptides may be prepared to have a stable cyclic structure by addition of cysteines at both ends, and also prepared in the form of a fusion protein with a carrier protein in order to acquire an effective expressome of the epitope.

As used herein, the term "carrier protein" means a protein or a fragment thereof that binds with a desired protein or polypeptide to effectively maintain the expression of an epitope. It may be GFP (green fluorescence protein), HSA (human serum albumin), MBP (maltose binding protein), or streptavidin but is not limited thereto, and specifically, it may be streptavidin. In the specific Example of the present invention, streptavidin showing no non-specific binding to human serum is used as the carrier protein to prepare the polypeptide of the present invention in the form of fusion protein, in order to increase sensitivity and specificity of a diagnostic kit.

Analysis methods for measuring the expression levels include, but are not limited to, Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, protein chip assay, etc. By the above detection methods, formation of antigen-antibody complex in a normal control group may be compared with that in individuals with liver cancer or suspected of having liver cancer, thereby diagnosing the incidence of liver cancer in patients suspected of having liver cancer.

The diagnostic method for liver cancer may be achieved by an antibody-antigen reaction between the anti-EIF3A autoantibody of the present invention and the antigen specifically binding thereto. As used herein, the term "antigen-antibody complex" refers to a binding product of the liver cancer marker, autoantibody and an antigen specific thereto. The amount of formed antigen-antibody complexes may be quantitatively determined by measuring the signal intensity of a detection label. Specifically, the antigen-antibody complex in the present invention may be a binding product of the anti-EIF3A complex and the antibody specific thereto.

Such a detection label may be selected from the group consisting of enzymes, fluorescent substances, ligands, luminescent substances, microparticles, redox molecules, and radioactive isotopes, but is not limited to thereto. Examples of enzymes available as detection labels include, but are not limited to, β-glucuronidase, β-D-glucosidase, β-D-galactosidase, urase, peroxidase or alkaline phosphatase, acetylcholinesterase, glucose oxidase, hexokinase and GDPase, RNase, glucose oxidase and luciferase, phosphofructokinase, phosphoenolpyruvate carboxylase, aspartate aminotransferase, phosphoenolpyruvate decarboxylase, and β-latamase. Examples of the fluorescent substances include, but are not limited to, fluorescein, isothiocyanate, rhodamine, phycoerythrin, phycocyanin, allophycocyanin, o-phthaldehyde, and fluorescamine. Examples of the ligands include, but are not limited to, biotin derivatives. Examples of luminescent substances include, but are not limited to, acridinium esters, luciferin, and luciferase. Examples of the microparticles include, but are not limited to, colloidal gold and colored latex. Examples of the redox molecules include, but are not limited to, ferrocene, ruthenium complexes, viologen, quinone, Ti ions, Cs ions, diimide, 1,4-benzoquinone, hydroquinone, $K_4W(CN)_8$, $[Os(bpy)_3]^{2+}$, $[RU(bpy)_3]^{2+}$, and $[MO(CN)_8]^{4-}$. Examples of the radioactive isotopes include, but are not limited to, $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Further, the present inventors demonstrated that the antibody specifically binding to anti-EIF3A may be used as a diagnostic marker for liver cancer by the following experiment.

First, spleen cells were obtained from a liver cancer mouse model as a parental cell, and fused with myeloma cells to produce B cell hybridomas. From the antibodies secreted by the produced hybridoma cells, antibodies showing reactivity with liver cancer cells were selected to isolate the XC90 clone-derived XC90mAb autoantibody of the present invention (FIG. 1).

Thereafter, the presence of antigen reacting with the isolated autoantibody was examined. For more specific analysis of the antigen, the isolated autoantibody XC90mAb was purified in a large amount, and mannose binding protein-agarose or protein L-agarose purification was performed to examine the intracellular localization of the antigen (expression in the cytoplasm) and identify the corresponding autoantigen proteins (FIG. 2). The kind and function of the identified antigen were examined, and as a result, the corresponding antigen was found to be EIF3A (FIGS. 2 and 3).

Figure 5A:
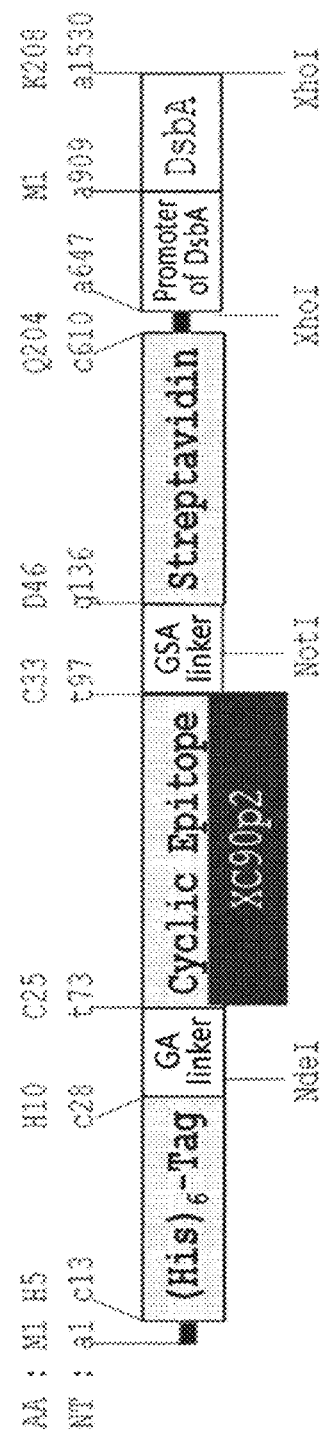
FIG. 5A is a schematic illustration showing a structure of a recombinant protein of "N terminal-linker-epitope-linker-mature streptavidin-C terminal" which was designed by using mature streptavidin as a carrier, placing 6× histidine tag for protein purification and cyclic epitope at the N-terminus, and adding linkers in order to minimize structural influence between domains.
Figure 5B:
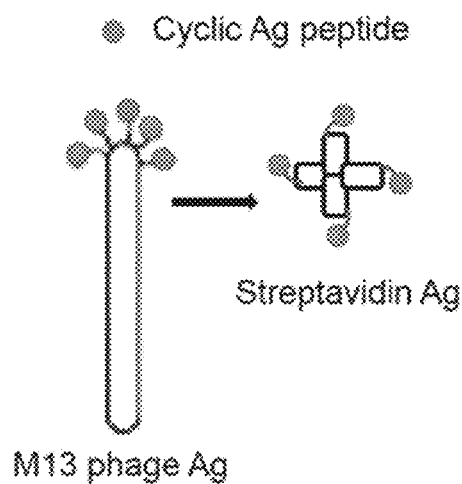
FIG. 5B is a schematic illustration showing that the recombinant protein was expressed in the form of having 4 antigens.
Figure 5C:
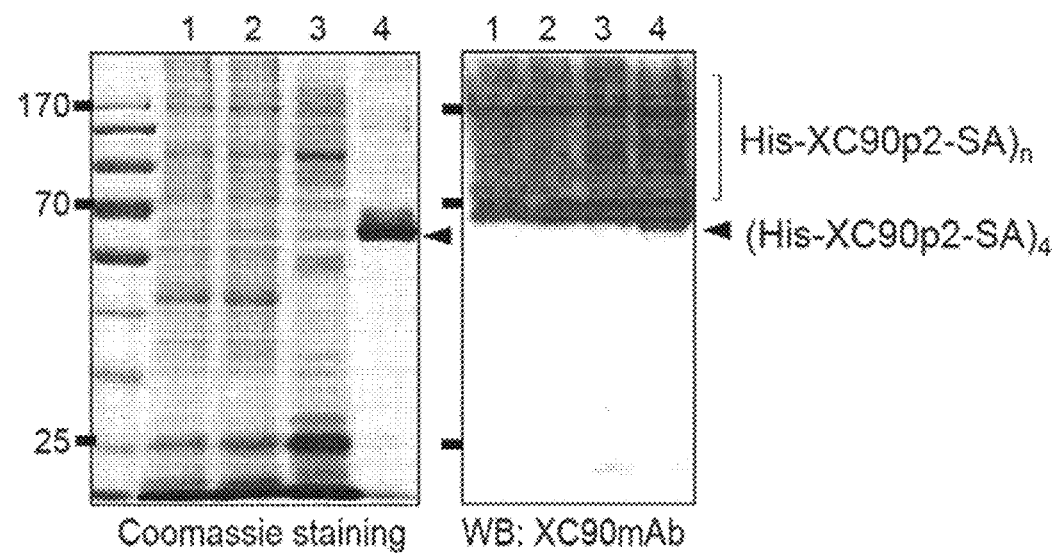
FIG. 5C is a photograph of Western blotting analysis showing the result of expressing the recombinant protein which was designed to have the structure of "N terminal-linker-epitope-linker-mature streptavidin-C terminal"

Furthermore, the present inventors examined a specific epitope sequence using a phage display-peptide library consisting of 7 amino acids, in order to identify the epitope sequence binding to the purified autoantibody (Table 1). ELISA was performed using the identified phage sequence as a coating antigen and the identified autoantibody as a primary antibody, so as to identify antigen groups showing high reactivity. An antigen showing the highest reactivity (identified by the phage library designated as XC90p2) was found and designated as XC90p2 antigen or XC90p2 autoantigen (FIG. 5).

In still another aspect, the present invention provides a kit for diagnosing liver cancer comprising the composition.

In the present invention, the antigen specifically binding to anti-EIF3A autoantibody includes all proteins capable of specifically binding to the autoantibody, and is not limited to particular proteins or polypeptides. Specifically, the antigen may include any fragment thereof or any variant thereof, as long as it may be recognized by the anti-EIF3A autoantibody. The antigen may be composed of 1 to 2000 amino acids, and with respect to the objects of the present invention, the antigen may be specifically composed of 5 to 16 amino acids, but is not limited thereto. More specifically, the antigen may be a protein including an epitope representing structure that may be recognized by the autoantibody marker of the present invention. The epitope is not particularly limited to its size or type, as long as the epitope can form a structure recognizable by the autoantibody of the present invention, and for example, the epitope may be a polypeptide consisting of 7 amino acids. For another example, the epitope may be a polypeptide represented by the amino acid sequences of SEQ ID NOS: 1 to 9. For example, the present inventors identified the sequence that is specifically recognized by the autoantibody of the present invention, by using $CX_7C$-peptide display phages. As a result, the autoantibody of the present invention was found to show high reactivity to the polypeptide represented by the amino acid sequence of SEQ ID NO: 2 (FIG. 4).

The diagnostic kit for liver cancer of the present invention may include not only a primer to measure the expression level of EIF3A as a diagnostic marker for liver cancer, a probe or an antibody selectively recognizing the marker but also one or more compositions of other components, a solution, or an apparatus, which are suitable for the analysis method.

Further, the kit for measuring the expression level of the protein expressed from the gene encoding the diagnostic marker EIF3A may include a matrix, a suitable buffer solution, a coloring enzyme, or a secondary antibody labeled with a fluorescent substance, a coloring substrate or the like for the immunological detection of the antibody. As for the matrix, a nitrocellulose membrane, a 96-well plate made of polyvinyl resin, a 96-well plate made of polystyrene resin, and a slide glass may be used. As for the coloring enzyme, peroxidase and alkaline phosphatase may be used. As for the fluorescent substance, FITC and RITC may be used, and as for the coloring substrate solution, ABTS (2,2'-azino-bis-(3-ethylbenzothiazoline-6-sulfonic acid)), OPD (o-phenylenediamine), or TMB (tetramethyl benzidine) may be used.

Analysis methods for measuring the protein level include, but are not limited to, Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, and protein chip assay, and specifically, the kit of the present invention may be a kit using ELISA coated with the anti-EIF3A complex.

The protein expression level may be measured by ELISA. ELISA includes various ELISA methods such as direct ELISA using a labeled antibody recognizing an antigen immobilized on a solid support, indirect ELISA using a labeled antibody recognizing a capture antibody in antibody complexes recognizing an antigen immobilized on a solid support, direct sandwich ELISA using another labeled antibody recognizing an antigen in an antigen-antibody complex immobilized on a solid support, and indirect sandwich ELISA, in which another labeled antibody recognizing an antigen in an antigen-antibody complex immobilized on a solid support is reacted, and then a labeled secondary antibody recognizing the former antibody is used. For example, the protein expression levels are detected by sandwich ELISA, where a sample reacts with an antibody immobilized on a solid support, and the resulting antigen-antibody complexes are detected by adding a labeled antibody specific to the antigen, followed by enzymatic color development, or by adding a labeled secondary antibody specific to the antibody which recognizes the antigen of the antigen-antibody complex, followed by enzymatic development. The incidence of liver cancer may be diagnosed by measuring the binding degree of the diagnostic marker EIF3A and the antibody.

In one Example of the present invention, the epitope sequence reacting with the autoantibody of the present invention was identified by using $CX_7C$-peptide display phage libraries, and reacted with a primary antibody, and then with IgGAM-HRP, followed by examination of the antigen-antibody complex formation and the amount thereof. As a result, there was a clear difference in the patterns between the sera of normal individuals and those of liver cancer individuals.

When detection of the anti-EIF3A autoantibody or diagnosis of liver cancer is performed in such a manner, liver cancer may be diagnosed with high specificity and sensitivity. In the preferred embodiment of the present invention, ELISA (Enzyme-linked immunosorbent assay) was used to perform the detection. As a result, individuals with liver cancer may be diagnosed and distinguished from normal individuals with 73.81% sensitivity and 76.74% reaction specificity.

Further, Western blotting may be performed by using one or more antibodies against the diagnostic marker. Total proteins are isolated from a sample, electrophoresed to be separated according to size, transferred onto a nitrocellulose membrane, and reacted with an antibody. The amount of proteins produced by gene expression is determined by measuring the amount of produced antigen-antibody complexes using a labeled antibody, thereby diagnosing the incidence of liver cancer.

In addition, immunohistostaining may be performed by using one or more antibodies against the marker. Tissue samples from liver cancer patients or individuals suspected of having liver cancer were collected and fixed, and then paraffin-embedded blocks were prepared according to a widely known method. The blocks were cut into small sections several μm in thickness, and attached to glass slides to be reacted with the fragment including the antigen-binding site of the autoantibody of the present invention according to a known method. Subsequently, the unreacted antibodies were washed, and the reacted antibodies were labeled with one selected from the above mentioned detection labels, and then observed under a microscope.

A protein chip, in which one or more antibodies against the marker are arranged and fixed at a high density at predetermined positions on a substrate, may be used. In this regard, in a method of analyzing a sample by using the protein chip, proteins are separated from the sample and hybridized with a protein chip to form an antigen-antibody complex, which is then read to examine the presence or expression level of the protein, thereby diagnosing the occurrence of liver cancer.

In still another aspect, the present invention provides a method of diagnosing liver cancer, including the step of detecting the autoantibody or the fragment including the antigen-binding site thereof by using the composition.

Specifically, the method of diagnosing liver cancer of the present invention may comprise the steps of (a) measuring an expression level of the autoantibody specifically binding to EIF3A protein or the fragment including the antigen-binding site thereof in a biological sample from a patient suspected of having liver cancer; and (b) comparing the expression level of the autoantibody or the fragment measured in step (a) with that of a biological sample separated from a normal individual.

As used herein, the term "individual" includes horses, dogs, cats, pigs, goats, rabbits, hamsters, monkeys, guinea pigs, rats, mice, lizards, snakes, sheep, cattle, fish, and birds without limitation, and means any animal (e.g., human), and widely includes cell lines of the animals without limitation.

In the present invention, the control group is a sample derived from an individual showing lower expression level of the anti-EIF3A autoantibody than that of an individual having liver cancer or suspected of having liver cancer, and refers to a sample to be used as a standard for the diagnosis of liver cancer by antigen-antibody reaction using the anti-EIF3A autoantibody of the present invention.

As used herein, the term "sample" refers to any one or more samples selected from the group consisting of whole blood, serum, blood, plasma, saliva, urine, sputum, lymphatic fluid, cerebrospinal fluid, and interstitial fluid that shows a difference in the expression levels of the anti-EIF3A autoantibody which is a diagnostic marker for liver cancer, but is not limited thereto.

Further, analysis methods of measuring the protein expression level include Western blotting, ELISA (Enzyme Linked Immunosorbent Assay), radioimmunoassay (otA), radioimmunodiffusion, Ouchterlony immunodiffusion, rocket immunoelectrophoresis, immunohistochemical staining, immunoprecipitation assay, complement fixation assay, FACS, and protein chip assay, but the methods of measuring the protein expression level are not limited to the examples.

In still another aspect, the present invention provides a method of screening for a therapeutic agent for liver cancer, the method comprising the steps of: (a) measuring an expression level of the autoantibody specifically binding to EIF3A protein in an individual; (b) administering a candidate therapeutic agent for liver cancer to the individual; (c) measuring an expression level of the autoantibody specifically binding to EIF3A protein in the individual administered with the candidate therapeutic agent; and (d) determining the candidate therapeutic agent as the therapeutic agent for liver cancer, when the expression level measured in step (c) is lower than the expression level measured in step (a).

In step (a), the step of measuring the expression level of the autoantibody specifically binding to EIF3A protein from an individual excluding humans may be performed by a method of measuring the expression level commonly used in the art without limitation, and examples thereof include Western blotting, ELISA (Enzyme Linked Immunosorbent Assay), radioimmunoassay (otA), radioimmunodiffusion, Ouchterlony immunodiffusion, rocket immunoelectrophoresis, immunohistostaining, immunoprecipitation assay, complement fixation assay, FACS, and protein chip assay.

Steps (b) and (c) include the steps of administering the candidate therapeutic agent for liver cancer to the individual and measuring the expression level of the autoantibody specifically binding to EIF3A protein in the individual administered with the candidate therapeutic agent, and step (d) is screening step that includes the step of determining the candidate therapeutic agent as the therapeutic agent for liver cancer, when the expression level measured in step (c) is lower than the expression level measured in step (a).

As used herein, the term "candidate therapeutic agent for liver cancer" refers to a substance expected to treat liver cancer. Any substance may be used without limitation, as long as it is expected to directly or indirectly ameliorate or improve liver cancer. It includes all candidate therapeutic substances such as compounds, genes or proteins. The screening method of the present invention examines the expression level of anti-EIF3A before and after administration of the candidate substance. When the expression level is decreased, as compared with the expression level before administration of the candidate therapeutic substance, the corresponding candidate therapeutic substance may be determined as a therapeutic agent for liver cancer Hereinafter, constitution and effects of the present invention will be described in more detail with reference to Examples. However, these Examples are for illustrative purposes only, and the scope of the present invention is not intended to be limited by these Examples.

Example 1: Acquisition of XC90 Autoantibody Derived from HBx Mouse

In order to acquire autoantibodies produced during carcinogenesis, an HBx transgenic mouse which develops liver cancer similar to human liver cancer was used. Spleen cells were obtained from HBx transgenic mice, in which development of liver cancer was confirmed, as a B cell group, and fused with a mouse myeloma cell Sp2/0 to prepare a B cell hybridoma cell line according to a common B cell hybridoma preparation method. Primary selection of the fused cells was performed using HAT medium (hypoxanthine-aminopterin-thymidine medium), and only clone-forming cells were cultured separately. The cells, in which cancer cell-reactive antibodies were detected in the culture medium of the clone-forming cells, were only selected and maintained.

The reactivity of cancer model mouse-derived autoantibodies against cancer cells was examined by flow cytometric analysis of cancer cell line after intracellular staining following the fixation and permeabilization. The method is described in detail as follows. A human liver cancer cell line HepG2 or a mouse liver cancer line Hepa1c1c7 was cultured until the number of cells reached 70-80% confluency in a culture plate, and then detached from the culture plate by trypsin treatment, and washed with a phosphate buffer solution (PBS). 100 µl of Cytofix/Cytoperm solution (BD Biosciences) per $2 \times 10^5$ cells was added thereto, and the cells were incubated at 4° C. for 20 minutes for fixation and permeabilization. After incubation, 1 ml of Cytowash/Cytoperm solution was added and mixed well. Then, cell precipitation was performed by centrifugation at 1,700 rpm for 5 minutes and the cell pellet was washed. 50 µl of a primary antibody solution (B cell hybridoma cell culture medium or purified primary antibody solution) was added to the washed sample, and the incubation was performed at 4° C. for 40 minutes. After incubation, the cells were washed three times, and treated with anti-mouse antibody-FITC (DaKo) at 4° C. for 40 minutes. Then, the cells were further washed three times, and the cell pellet was resuspended in 300 µl of PBS, followed by analysis using a FACSCaliber (BD Biosciences). Mean values of fluorescence corresponding to antibody reactions were obtained and compared. Primary antibody-free DMEM medium was used as a control group showing no antibody reaction.

As a result, many autoantibody-producing clones were obtained. Among them, a XC90 clone-secreting antibody was investigated in the present invention.

The hybridoma cell line producing the XC90 clone-secreting antibody was deposited at the Biological Resource Center (KCTC), Korea Research institute of Bioscience and Biotechnology (KRIBB) under the Accession No. KCTC 12590BP on May 12, 2014.

Example 2: Determination and Purification of XC90 Antibody Isotype

An isotype of XC90 antibody was determined by analysis using a mouse antibody isotyping kit, and as a result, it was IgM type.

For analysis of XC90 antibody-specific reaction, a monoclonal antibody was purified. Cell culture medium obtained by culturing a large amount of XC90 antibody-producing B cells or an antibody-producing cell was injected into the peritoneal cavity of mice, thereby acquiring ascites fluid. The ascites fluid was applied to mannose-binding protein-agarose (Pierce) or protein L agarose to purify IgM type antibody.

After SDS-PAGE, the purified antibodies were confirmed by Coomassie staining, and protein quantification was performed by a Bradford method.

Example 3: Expression of XC90 Antibody-Specific Antigen in Various Cancer Cells and Identification of Antigen Protein To examine reactivity of the XC90 monoclonal autoantibody purified in Example 2 for various cancer cell lines, intracellular staining of the various cancer cell lines was performed in the same manner as in Example 1, followed by flow cytometry (FIG. 1A). As shown in FIG. 1A, expression of XC90 antibody-reactive antigen was observed in liver cancer cell lines including HepG2, SK-Hep-1, Huh7, etc., and other cancer cell lines including HeLa, HT29, etc., and in particular, overexpression of the autoantibody was observed in SK-Hepl liver cancer cell line and LNCap/LN3 prostate cancer cell line.

Figure 1B:
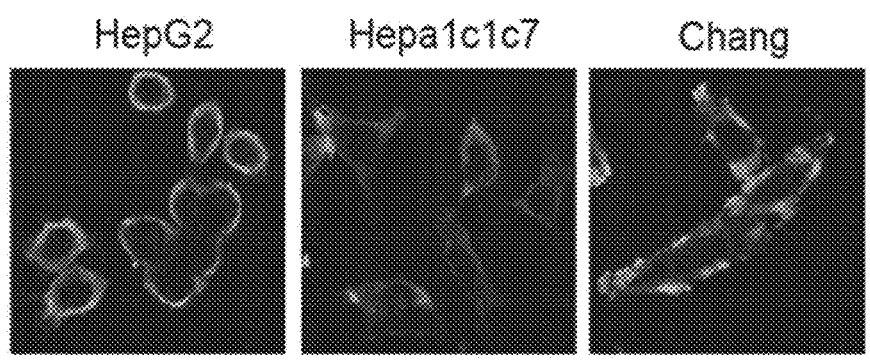
FIG. 1B is a microscopic image showing results of examining reactivity of XC90 antibody against various cancer cells by intracellular staining.

Further, to examine the intracellular localization of the antibody-reactive antigen expression in cells, confocal microscope was used to observe the cells after intracellular staining, and as shown in FIG. 1B, strong staining was observed in the cytoplasm.

Expression of the XC90 antibody-specific antigen protein was examined by Western blotting. The detailed method is as follows. The cultured cancer cell lines were collected and dissolved in NP40 cell lysis buffer (PBS containing 1.0% (v/v) NP40 and protease inhibitor cocktail (Roche)) and centrifuged at 13,000 rpm. The supernatants were used as protein analysis samples. Protein quantification was performed by Bradford assay. Each 50 µg of the prepared protein samples was run on 10% reduced SDS-PAGE, and transferred onto a PVDF membrane. Thereafter, the membrane to which proteins were transferred was blocked in a 5% (w/v) skim milk/TBS(Tris-buffered saline), and treated with a primary antibody. Purified XC90 antibodies were diluted in the blocking solution at a concentration of 0.1 µg/ml, and then used as the primary antibody. After treatment of the primary antibody, the antibodies were thoroughly washed with TBST (TBS containing 0.1% (v/v) tween-20), and treated with anti-mouse IgGAM-HRP as a secondary antibody. Subsequently, the antibody-reactive protein bands were detected by ECL (enhanced chemiluminescence). As shown in FIG. 1C, the XC90 antibody-specific antigens were found in HepG2 and Hepa1c1c7 cells as each band having a molecular weight of 150 kDa and 180 kDa.

Example 4: Identification of XC90 Antibody-Specific Protein

In order to examine whether production of the autoantibody against XC90 antigen is meaningful as a cancer biomarker, XC90 antigen protein was identified and its function was examined. The detailed method is as follows.

Figures 2A, 2B:
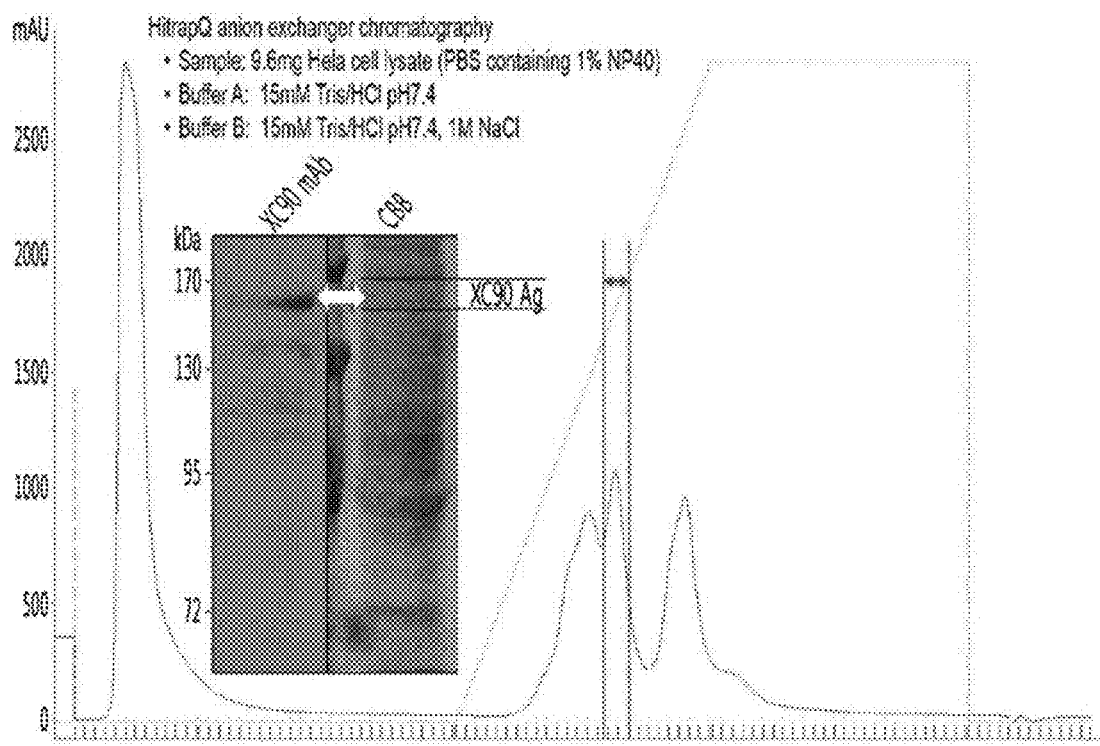
FIG. 2A is a photograph and a graph showing results of protein identification, in which only a fraction including a large amount of XC90 antibody-specific antigen protein was concentrated and run on SDS-PAGE, and a band corresponding to XC90 antigen was extracted, followed by in-gel digestion and mass spectrometry.
FIG. 2B is a table showing result of mass spectrometry of the obtained XC90 antibody-specific antigen protein.

As shown in FIG. 2A, for analysis of XC90 antibody-specific antigen protein, the antigen protein was partially purified from the expression cell line. To extract the protein, HeLa cell lysate (NP40 buffer used) showing high expression of the corresponding antigen protein was fractionated by ion exchange resin chromatography. HiTrap-Q (GE) column was used as an ion exchange resin, and fractionation was performed while increasing NaCl concentration. Based on the results of Western blotting of each fraction with XC90 antibody, a fraction containing the XC90 antibody-specific antigen protein was selected, and the selected fraction was collected and concentrated by acetone precipitation, and separated on 10% SDS-PAGE, followed by Western blotting and Coomassie staining for comparison. A protein band corresponding to XC90 antigen was cut out, and the cut protein band was subjected to in-gel digestion using trypsin protease. As shown in FIG. 2B, after reaction, the extracted peptide fraction was subjected to mass spectrometry to obtain information regarding the protein sequence. It was confirmed that the XC90 antibody-specific antigen was EIF3A (or called EIF3, eIF3a, eIF3 p167, eIF3-p170, eIF3 p180, eIF3 p185, EIF3S10, eIF3-theta, eIF-3-theta, eukaryotic translation initiation factor 3 subunit 10, eukaryotic translation initiation factor 3 subunit A, KIAA0139, P167, p180, p185, TIF32).

Figure 3A:
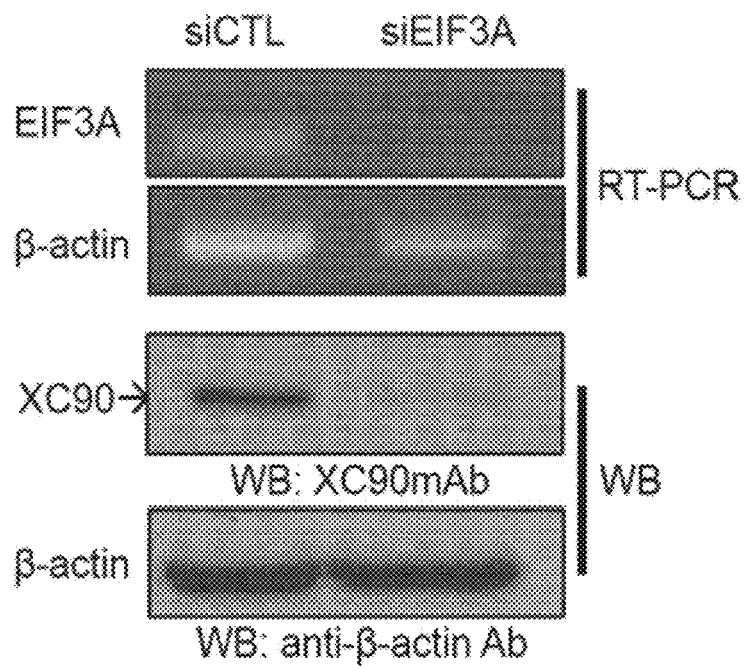
FIG. 3A is a photograph showing results of RT-PCR and Western blot analysis, in which expression of XC90mAb-binding antigen was reduced due to suppression of EIF3A expression by siRNA.
Figure 3B:
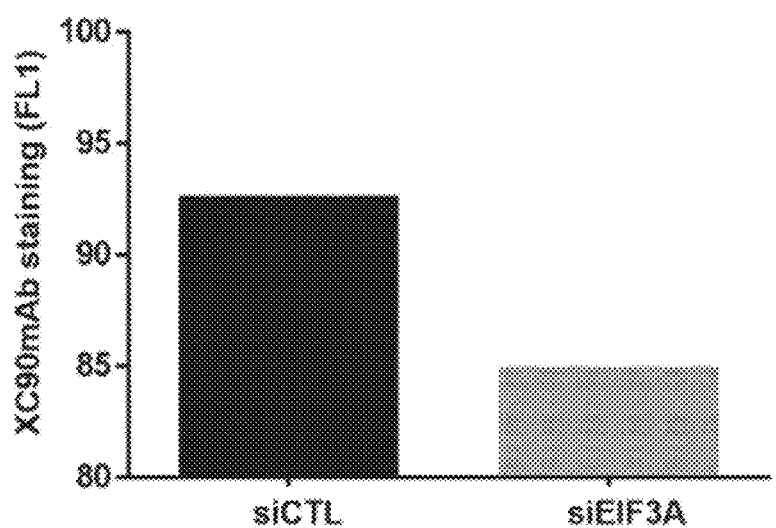
FIG. 3B is a graph showing results of flow cytometry, in which expression of XC90mAb-binding antigen was reduced due to suppression of EIF3A expression by siRNA.
Figure 3C:
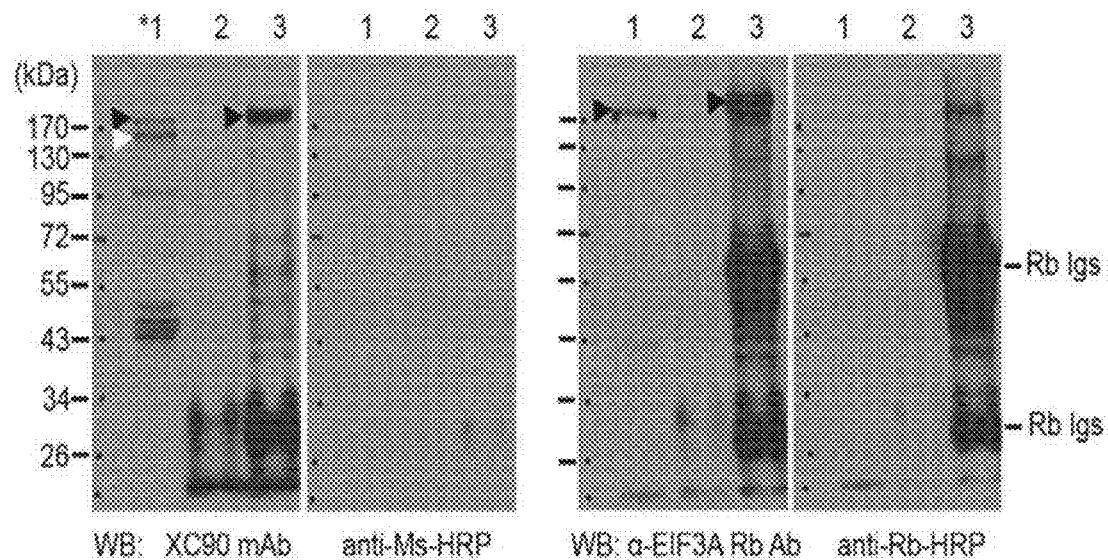
FIG. 3C is a photograph showing results of Western blot analysis of EIF3A protein by using XC90 antibody and EIF3A antibody as primary antibodies, after separating the EIF3A protein from a cell lysate by immunoprecipitation with EIF3A antibody and running the EIF3A protein on SDS-PAGE.

In order to confirm the result of the protein identification by mass spectroscopy, a reduction in XC90 antibody reaction was examined in the cells of which the expression of EIF3A was suppressed by using siRNA. As the siRNA (Bioneer) for the suppression of EIF3A expression, RNAiMAX (Invitrogen) were used and injected into HepG2 cells. 48 hours after siRNA treatment, the cells were collected to extract total RNA, and 5 µg of RNA was used as a template to synthesize cDNA. The synthesized cDNA was used as a template to perform PCR using EIF3A gene-specific primers. The resulting product was analyzed on a 1% agarose gel. The cells showing the suppressed EIF3A expression by siRNA treatment were subjected to Western blotting with XC90 antibody. As a result, as shown in FIG. 3A, the amount of the XC90 antibody-reactive antigen protein was remarkably reduced. Further, as shown in FIG. 3B, the result of flow cytometry after intracellular staining of the siRNA-treated cells with XC90 antibody showed that XC90 antibody-specific reaction was reduced upon suppression of EIF3A expression. Immunoprecipitation was performed to further confirm that EIF3A is a target of XC90 antibody. Anti-EIF3A antibody (Cell signaling) was bound to 50 µl of a protein A/G resin (Santa Cruz), and then 1 mg of cancer cell lysate was added thereto, and allowed to react at 4° C. for 16 hours. The antibody-antigen complex-resin was separated by centrifugation, washed with six times, and separated on a 10% SDS-PAGE, followed by Western blotting with anti-EIF3A antibody (Cell signaling) or XC90 antibody. As a result, as shown in FIG. 3C, it was confirmed that the two antibodies detected the same size of the protein. In FIG. 3C, Lane 1 represents the cell lysate used in immunoprecipitation, Lane represents a fraction immunoprecipitated with non-EIF3A antibody-bound resin, and Lane 3 represents a fraction immunoprecipitated with EIF3A antibody-bound resin.

Figure 3D:
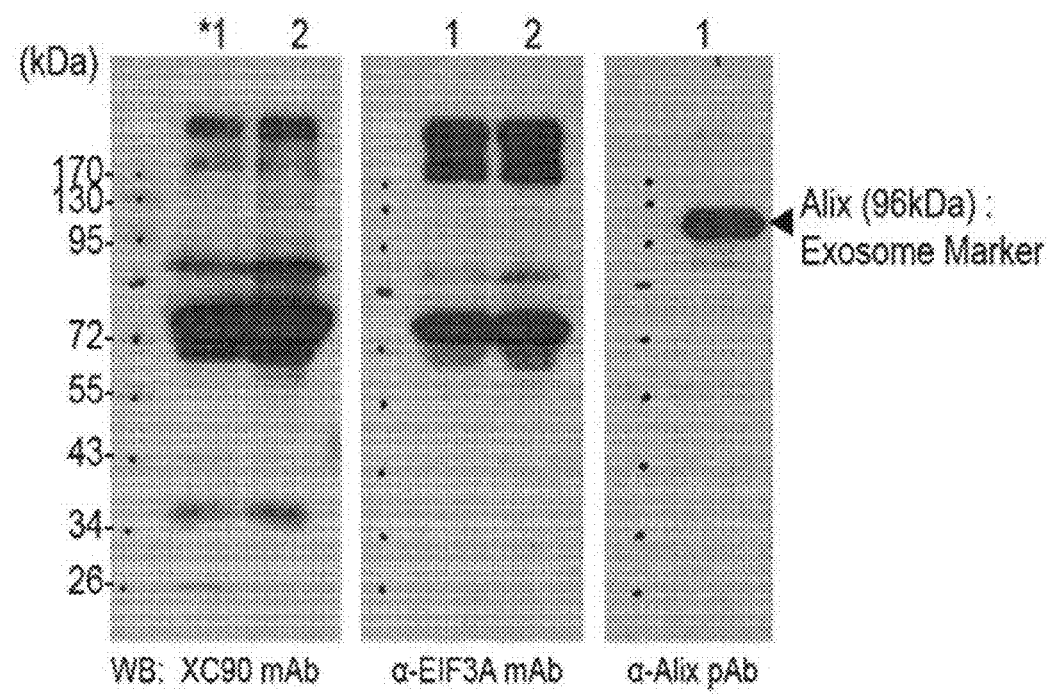
FIG. 3D is a photograph showing results of Western blot analysis, in which XC90mAb-specific antigen, EIF3A was found in a fraction of exosome released from cells.

When an antigen inducing an autoantibody is an intracellular protein, the antigen should be released from cells in order to stimulate the immune system. As a result of previous studies of the present inventors, most autoantibody-inducing antigens are exosomal proteins which are included in exosomes and then released from cells, and thus it was examined whether the XC90 antigen is also an exosomal protein. After collecting the HepG2 cell culture, exosomes were isolated by using an exosome isolation kit (Invitrogen), followed by Western blotting with XC90 antibody and anti-EIF3 antibody (Cell signaling). As a result, as shown in FIG. 3D, it was confirmed that the two antibodies recognized the same protein. In this regard, Sample 1 represents exosomes derived from HepG2 cells, and Sample 2 represents exosomes derived from Hepa1c1c7 cells.

These results confirmed that XC90 antibody-specific antigen is EIF3A, which is expressed inside cells and released from the cells in the form of exosome.

Example 5: Screening of XC90 Antibody-Specific Epitope

Since an antibody-inducing site in an antigen protein structure is extremely restricted and it commonly acts irrespective of an immunization host such as humans, rabbits, or mice, it was expected that the autoantibody acquired in the cancer mouse model is also induced in human carcinogenesis. Based on this feature, the present inventors expected that the autoantibody acquired in the cancer mouse model is also induced in human carcinogenesis, and they constructed a detection method of detecting a human cancer-derived autoantibody by acquiring an epitope specific to the autoantibody derived from the cancer mouse model. To acquire the epitope specific to the autoantibody derived from the cancer mouse model, cyclic peptide-expressing phage libraries were explored by using the autoantibody to select only the antibody-reactive phages, and their epitope sequences were confirmed. Competitive inhibition of antibody reaction for cancer cell-expressed antigens were confirmed, and it was confirmed that the epitope sequences may be used as an antibody-specific antigen mimetic. The detailed method is as follows.

Figure 4A:
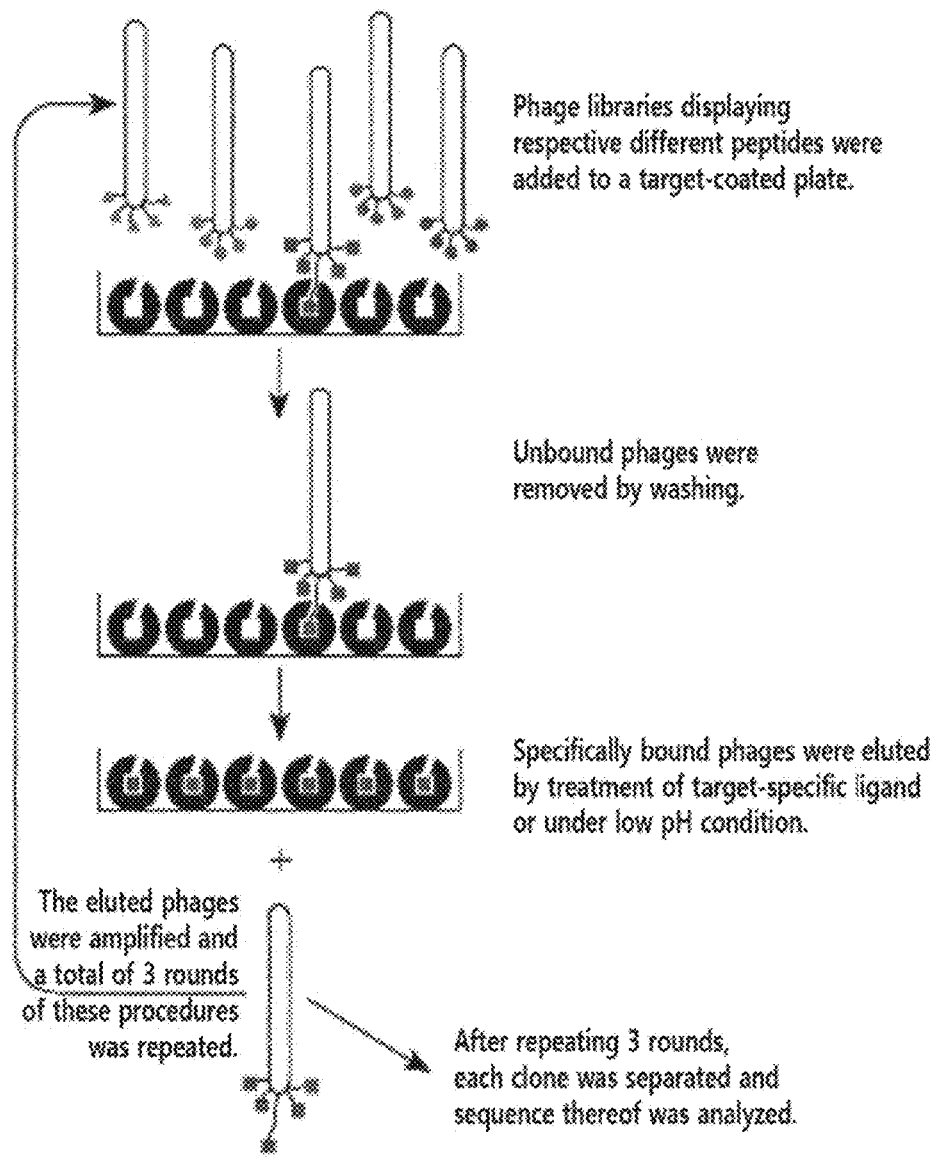
FIG. 4A is a schematic illustration showing a method of selecting XC90 antibody-specific antigen expressing phages by screening phage-display cyclic $CX_7C$-peptide libraries with XC90 antibody.
Figure 4B:
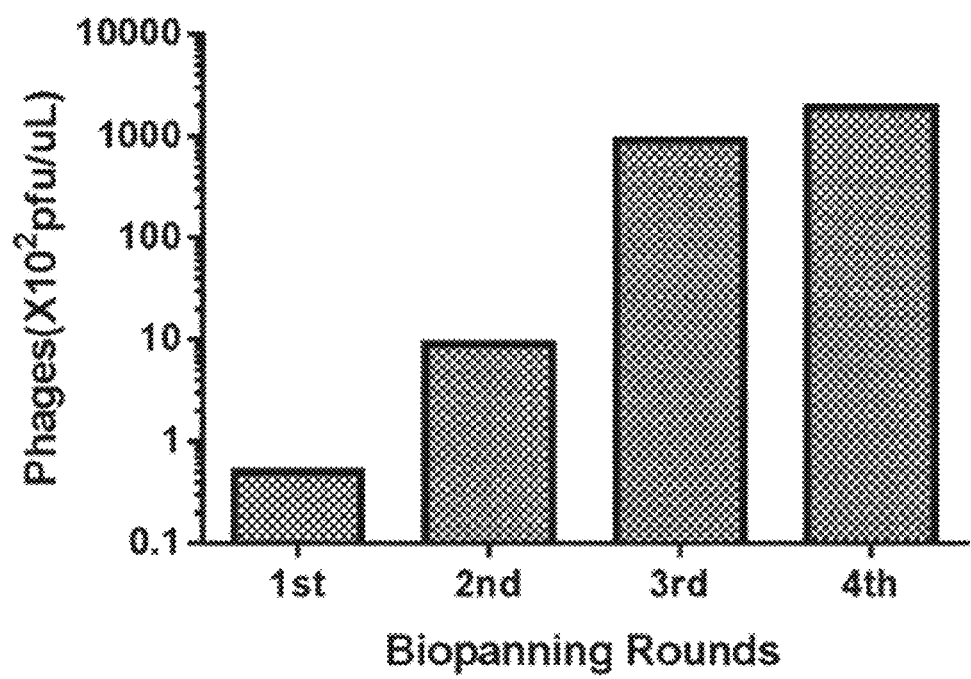
FIG. 4B is a graph showing results of four rounds of selection of XC90 antibody-specific antigen expressing phages.

In order to use a reactive site with ease rather than the entire antigen protein as the XC90 antibody-specific antigen, XC90 antibody-specific peptide antigens were screened from a peptide random expression library, as shown in FIG. 4A. Phase expressing cyclic peptide library kit (New England Biolabs), in which there are 7 amino acids randomly expressed and two additional cysteine residues at both termini to form a cyclic structure ($—CX_7C—$), was used as the peptide expression library. The panning was performed in accordance with the manufacturer's instructions as follows: 300 ng of XC90 antibody and phage virions expressing $2 \times 10^{11}$ different peptides were mixed with each other in 200 µl of TBST solution, and allowed to react at room temperature for 20 minutes. The mixture was mixed with 25 µl of protein L-agarose bead pre-treated with a blocking solution (0.1 M NaHCO$_3$, pH 8.6, 5 mg/ml BSA, 0.02% (w/v) NaN$_3$) and allowed to react at room temperature for 15 minutes. The reactive phages were subjected to centrifugation, and a cell pellet was recovered in a form of antibody-phage-protein L agarose conjugate. The cell pellet was washed with TBST several times, and eluted using 1 ml of elution buffer at pH 2.2 (0.2 M Glycine-HCl, pH 2.2, 1 mg/ml BSA). Immediately, 1 M Tris-HCl solution at pH 9.1 was added thereto for pH neutralization. A part of the eluted phages was used for phage titration, and the rest was used for phage amplification. The amplified phages were subjected to panning in the same manner as above. During the panning using XC90 antibody, the number of the amplified phage was increased at each round after the fourth round of panning. As shown in FIG. 4B, the results suggest amplification of XC90 antibody-specific phages. 9 phages were randomly selected from the phages obtained from the fourth round of panning, the epitope sequences of the peptides were determined by DNA sequencing analysis, and 9 different sequences determined therefrom are summarized in Table 1.

TABLE 1

Amino acid sequence of EIF3A peptide epitope

| Phage | Epitope sequence |
|---|---|
| XC90p1 | FPFPSSL (SEQ ID NO: 1) |
| XC90p2 | PVRSGFP (SEQ ID NO: 2) |
| XC90p3 | LPWPSSL (SEQ ID NO: 3) |
| XC90p4 | PSRHSGW (SEQ ID NO: 4) |
| XC90p5 | PSRHSGY (SEQ ID NO: 5) |
| XC90p6 | PARHSGF (SEQ ID NO: 6) |
| XC90p7 | PARTSWP (SEQ ID NO: 7) |
| XC90p8 | PPRTGFQ (SEQ ID NO: 8) |
| XC90p9 | PARSGYP (SEQ ID NO: 9) |

Figure 4C:
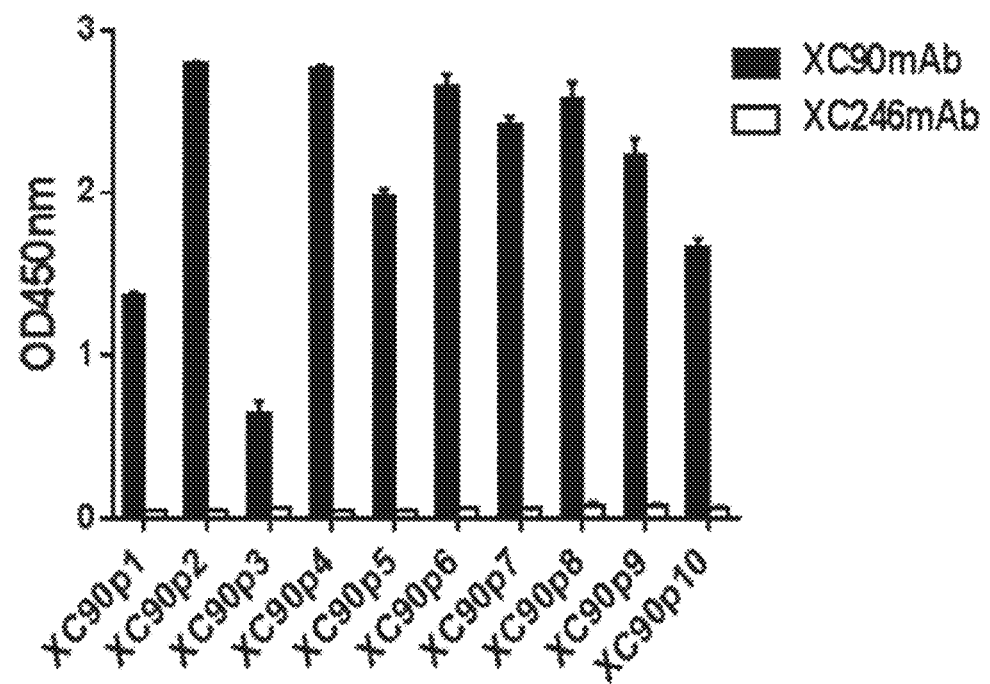
FIG. 4C is a graph showing results of ELISA for examining reactivity of XC90 antibody-specific antigen for XC90 antibody.
Figure 4E:
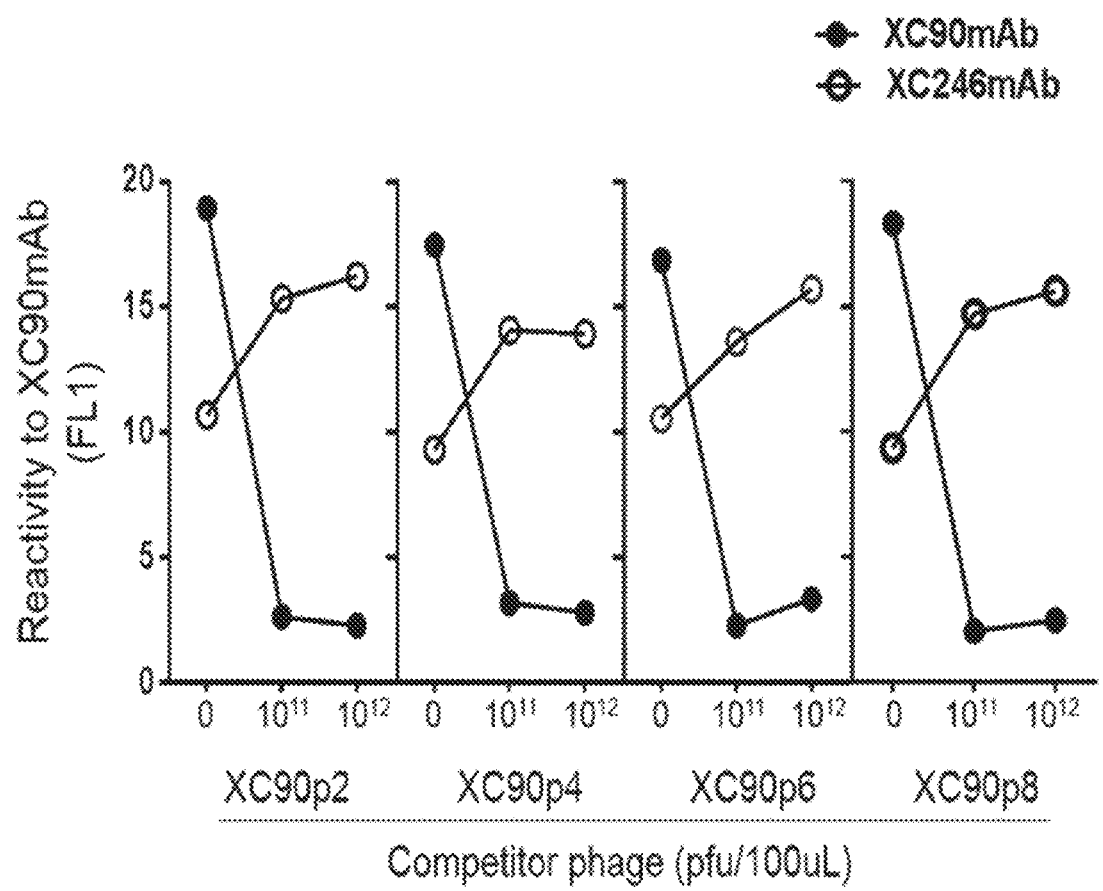
FIG. 4E is a graph showing results of analyzing reactivity to cells after previously reacting $10^{11}$ pfu or $10^{12}$ pfu of XC90 antibody-specific antigen expressing phage with XC90 antibody.

In order to examine the binding specificity of the selected phages against XC90 antibody, ELISA was performed. Each of the selected nine epitope-expressing phages was transfected into host cells, amplified, partially purified using a PEG/NaCl solution, and then used as an ELISA coating antigen. $10^{10}$ of the purified phage was diluted in 100 µl of a coating solution (0.1 M sodium bicarbonate buffer, pH 8.6) and added to each well of 96-well Maxisorp ELISA plate. For antigen coating, the phage-added plate was stored at 4° C. for 16 hours or longer. After phage coating, 300 µl of skim milk solution (5% (w/v) skim milk/TEST) was added, and allowed to react at room temperature for 1 hour to block the remaining sites after antigen coating. After blocking, the plate was washed with TEST twice, and 100 ng/100 µl of XC90 monoclonal antibody was added thereto, and allowed to react at room temperature for 90 minutes. Thereafter, the plate was washed with TBST six times, and treated with a secondary antibody, anti-mouse IgGAM-HRP (Pierce) diluted at a ratio of 1:2500. The secondary antibody was also reacted at room temperature for 90 minutes, and the plate was washed with TEST six times. Color development of HRP enzyme was performed by using a TMB solution (Pierce). Absorbance was measured at 450 nm to quantify the antigen-antibody reaction. As a result, as shown in FIG. 4C, among the nine phages used as an antigen, XC90p2, XC90p4, XC90p6, and XC90p8 showed high reactivity. By listing the selected phage antigens according to the order of antibody reactivity, sequence characteristics important for antibody reactivity were confirmed, and as shown in FIG. 4D, it was confirmed that a sequence characteristic of P-x-R-x-G-x-P (P: proline, x: non-specific amino acid, P: proline, R: arginine, G: glycine) is important for 7 amino acids. Particularly, in order to examine whether the epitope properly mimics the cancer cell-expressed antigen structure, competitive inhibition of antibody reaction by addition of the epitope-expressing phage was examined during analysis of cell reactivity of the autoantibody. $10^{11}$ or $10^{12}$ pfu of the phage antigen was added and inhibition of antibody reaction was examined. As a result, as shown in FIG. 4E, the reaction against XC90 antibody was completely inhibited, whereas the reaction against XC246 antibody which is an antibody having no specificity was not inhibited, and as the number of the phage was increased, the non-specific reaction was increased. These results suggest that the phage antigen epitope sufficiently mimics the cancer cell-expressed antigen epitope. Sequence characteristics thereof were analyzed, and as a result, it was confirmed that the epitope having high reactivity had a repeated structural characteristic. In the following Example, the sequence of XC90p2 was used as an epitope to analyze reactivity against human serum.

Example 6: Preparation of XC90p2 Epitope Expressome

In order to utilize the phage-expressed XC90p2 antigen in ELISA for serum analysis, continuous phage amplification and purification are required. For large-scale serum analysis, however, a process of acquiring the phage antigens has not been reproducibility repeated and quantity of the phage that can be obtained at a time was very small. For this reason, to replace M13 phage by an epitope carrier which is able to effectively express the autoantibody-reactive epitope and is stably purified and acquired, many different carrier proteins were tried. As a result, streptavidin was used as the epitope carrier, and primer sequences for the preparation of each expressome are listed in Table 2.

TABLE 2

Primer sequences used for preparation of epitope expressome

| Type of gene | Primer (5'-3') |
|---|---|
| Streptavidin | F: gcg gcc gca ggt tcg ggt tcg gcc- GAC CCC TCC AAG GAC TCG (SEQ ID NO: 10) |
| | R: ctc gag tca tca CTG CTG AAC GGC GTC GAG (SEQ ID NO: 11) |

TABLE 2-continued

Primer sequences used for preparation of epitope expressome

| Type of gene | Primer (5'-3') |
|---|---|
| XC90p2 epitope | F: tatgggtggtGCGTGCCCGGTTCGTTCTGGTTTCCCGtgcggtggaggttcggc (SEQ ID NO: 12)<br>R: ggccgccgaacctccaccgcaCGGGAAACCAGAACGAACCGGGCACGCaccaccca (SEQ ID NO: 13) |
| Eph-STA | F: cat atg ggt ggt gcg gcc gca ggt tcg ggt (SEQ ID NO: 14)<br>R: ctc gag tca tca CTG CTG AAC GGC GTC GAG (SEQ ID NO: 15) |
| DsbA | F: ctc gag cac cac cac cac cac cac tga tga att att gaa gct tat gaa gaa ttt (SEQ ID NO: 16)<br>R: ctc gag tta tta ttt ttt ctc gga cag ata tt (SEQ ID NO: 17) |

Figure 6A:
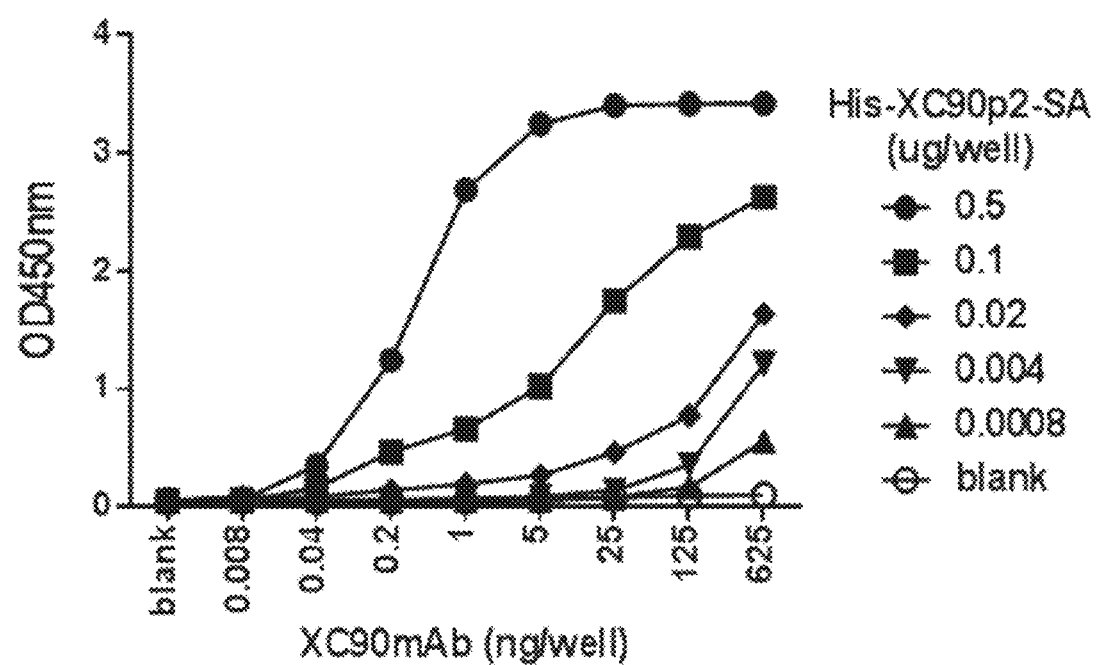
FIG. 6A is a graph showing the result of examining whether the recombinant protein His-XC90p2-SA having XC90p2 epitope is effective for the autoantibody detection, in which a biotin plate was coated with purified His-XC90p2-SA protein at different concentrations, and reacted with XC90mAb at different concentrations to examine the degree of specific reaction.

The detailed method is as follows: As shown in FIG. 5A, in order to prepare a gene expressing a streptavidin protein containing the XC90p2 antigen epitope, cloning was performed to have a sequence of 'N terminal-linker-epitope-linker-streptavidin-C terminal'. For cloning of mature streptavidin gene, colony PCR was performed by using *Streptomyces avidinii* culture colony as a template, specific primers (SEQ ID NOS: 10 and 11), and nPfu DNA polymerase (Solgent). The amplified streptavidin gene was cloned into a pTOP Blunt V2 vector (Enzynomics), followed by sequencing analysis. The streptavidin gene thus obtained was cloned into a pET28a(+) vector (Novagen) by using restriction enzymes, NotI and XhoI.

To prepare the XC90p2 epitope sequence, primers containing a linker sequence such as SEQ ID NOS: 12 and 13 were synthesized. Each primer was reacted with T4 polynucleotide kinase (Takara) at 37° C. for 1 hour to phosphorylate 5'-terminus, and then mixed. PCR was performed to react the primers at 95° C. for 5 minutes, which were then slowly cooled to prepare the XC90p2 epitope gene. To prepare a final XC90p2 epitope-expressing carrier, an expression vector having the streptavidin gene was digested with NdeI and NotI restriction enzymes, and then mixed with the XC90p2 epitope gene at a predetermined ratio. Ligase (Roche) was added to the mixture, and ligation was allowed at 16° C. for 16 hours. The ligation mixture was transformed into DH5α, and spread on an LB defined medium plate containing Kanamycin, followed by incubation at 37° C. for 15 hours. Colonies on the plate were selected, and cultured in LB defined liquid medium. The amplified recombinant plasmid was isolated, followed by sequencing analysis. As shown in FIG. 5A, an XC90p2 epitope-expressing carrier vector having the structure of 'N terminal-linker-epitope-linker-streptavidin-C terminal' was obtained.

As a control group of the XC90p2 epitope-expressing protein, Eph-STA expressing only linker and streptavidin without the epitope was prepared and used. Eph-STA gene was obtained by PCR using the streptavidin template vector and primers (SEQ ID NOS: 14 and 15), and cloned in the same manner as in the cloning of the XC90p2 epitope-expressing carrier to obtain the control protein (Eph-STA)-expressing vector.

Formation of a cyclic peptide structure by cysteines at both ends of the epitope sequence is essential for maintaining the antibody reactivity of the epitope. Rosetta gami TMB (Novagen) strain having improved expression of enzymes involved in disulfide bond formation was used as a host for expression of the XC90p2 epitope carrier, and disulfide oxidoreductase DsbA (Gene ID: 8114936) was additionally expressed so that disulfide bond formation was favored. As shown in FIG. 5A, cloning of the DsbA gene was performed as follows: The primers (SEQ ID NOS: 16 and 17) were prepared to have the 414th upstream sequences from the initiation codon so that the promoter region of DsbA was included. PCR was performed by using gDNA of BL21 strain as a template and nPfu DNA polymerase (Solgent). The obtained DsbA gene and XC90p2-mature streptavidin sequence-containing pET28a(+) vector (Novagen) were digested with restriction enzyme (XhoI) at 37° C. for 4 hours, and then the digested vector and the obtained DsbA gene were mixed at a predetermined ratio. Ligase (Roche) was added thereto, and ligation was allowed at 16° C. for 16 hours. The ligation mixture was transformed into DH5α, and spread on an LB defined medium plate containing Kanamycin, followed by incubation at 37° C. for 12 hours or more. Colonies on the plate were selected, and cultured in LB defined liquid medium. The amplified recombinant plasmid was isolated, followed by sequencing analysis.

Example 7: Expression and Purification of XC90p2 Recombinant Protein

His-XC90p2-SA recombinant protein was obtained by transforming the XC90p2 epitope expression vector (His-XC90p2-SA/pET28a(+)) into Rosetta gami TMB (Novagen) strain, and then culturing the strain with addition of IPTG (isopropyl β-D-1-thiogalactopyranoside) at a final concentration of 1 mM at 25° C. for 20 hours.

The cultured cells were suspended in a Sepharose-Q column binding buffer (20 mM of Tris-HCl at pH 8.0), and sonicated, followed by centrifugation. Partial purification was performed by anion exchange resin chromatography of slowly applying the supernatant to a Sepharose-Q column at 4° C., and applying an elution buffer (20 mM of Tris-HCl at pH 7.4, 1 M of NaCl) thereto. XC90 antibody reactive fraction was mixed with a Talon resin (Clontech) column buffer (50 mM of Tris-HCl at pH 7.4, 150 mM of NaCl, 25% glycerol) at a ratio of 1:1, and the mixture was slowly added to the Talon resin at 4° C. Thereafter, the column was washed with a column buffer to remove non-specific proteins. An elution buffer (50 mM of Tris-HCl pH 7.4, 150 mM of NaCl, 25% glycerol, 2 mM PMSF, 10 mM of imidazole) was treated thereto to perform elution and purification. As shown in FIG. 5C, protein purity at each purification step was examined by running on non-heated/non-reduced SDS-PAGE, and Coomassie staining and Western blotting. As a result, as shown in FIG. 5B, a high-purity protein antigen having a molecular weight of tetrameric streptavidin or higher was isolated.

Example 8: Examination of XC90 Autoantibody Reactivity by Using XC90p2-Expressing Recombinant Protein and Competitive Inhibition for Cancer Cell Reaction In order to examine reactivity of the obtained antigen against the autoantibody, ELISA was performed. A biotin plate was coated with purified His-XC90p2-SA protein at different concentrations, and reacted with different concentrations of XC90mAb to examine the degree of specific reaction. As a result, as shown in FIG. 6A, when the antigen was coated at a concentration of 0.5 µg/well, the autoantibody XC90mAb was detected up to 0.04 ng/100 µl.

Figure 6B:
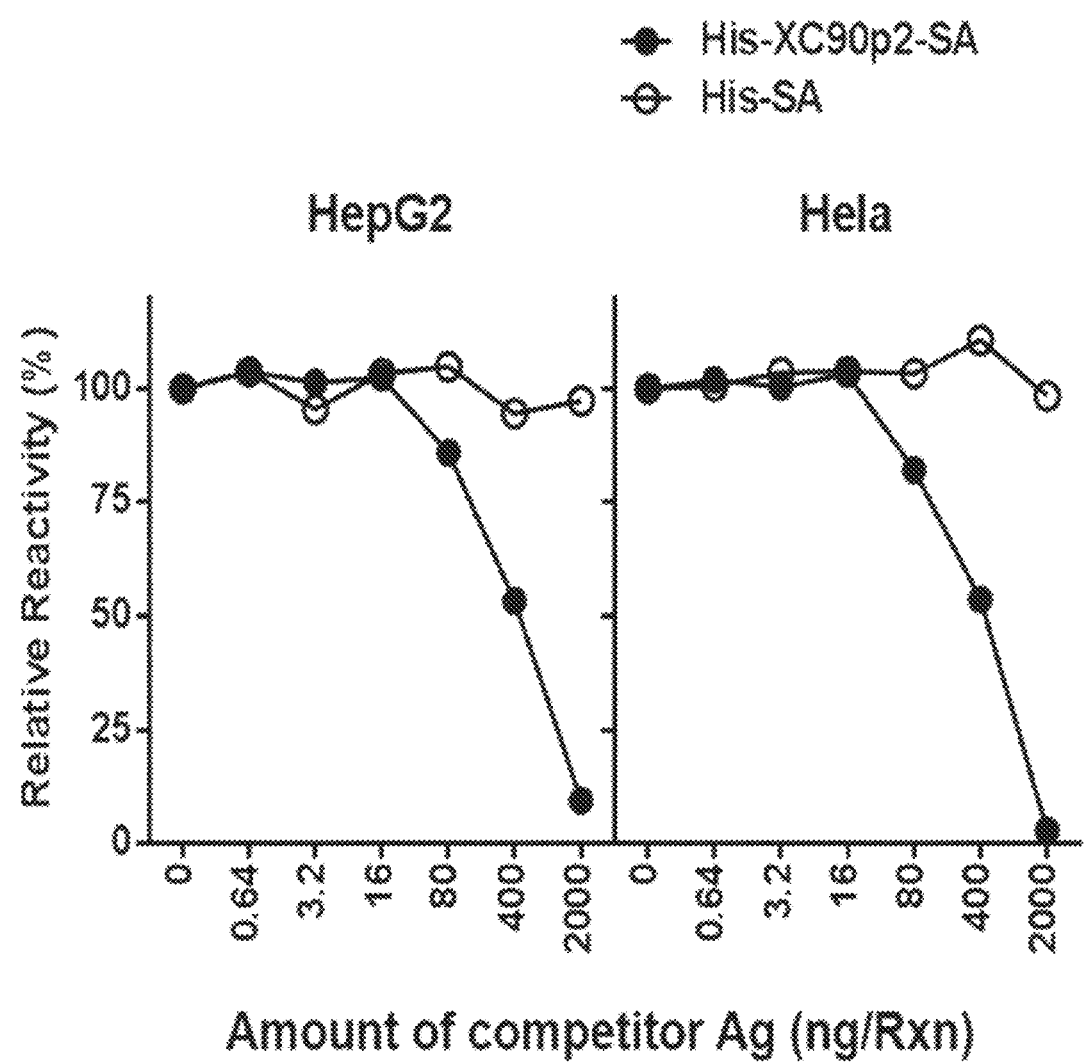
FIG. 6B is a graph showing the result of examining whether the recombinant protein His-XC90p2-SA having XC90p2 epitope properly mimics the cell-expressed antigen, in which competitive inhibition of cell reaction of the XC90 antibody was examined.

Further, in order to examine whether the antibody-specific epitope-expressing recombinant protein sufficiently mimics the epitope of the cancer cell-expressed antigen protein, when the reaction of the XC90 antibody and the cell-expressed antigen protein was measured by flow cytometry, the XC90 antibody-specific recombinant protein was added to examine whether the reaction was competitively inhibited. Flow cytometry was performed in the same manner as in Example 1. As a primary antibody, XC90 antibody was treated alone, or XC90 antibody was previously mixed and reacted with the purified His-XC90p2-SA recombinant protein for 1 hour, and then treated. These two cases were compared with each other. Each 0.2 µg of the antibody was used, and 0.108 ng to 2 µg of the recombinant protein was used. As a control group, His-Eph-SA recombinant protein expressing no antigen peptide was used, and reactivity in HepG2 and HeLa cells was examined. As a result, as shown in FIG. 6B, it was confirmed that the His-XC90p2-SA recombinant protein inhibited reaction of the XC90 antibody against antigens present in HepG2 or HeLa cells in a recombinant protein concentration-dependent manner. However, His-Eph-SA did not inhibit the antibody reaction. These results suggest that the His-XC90p2-SA recombinant protein sufficiently mimics the epitope of the XC90 antibody-specific antigen protein.

Example 9: Diagnosis of Human Liver Cancer by Using XC90p2 Epitope-Expressing Recombinant Protein An epitope of a protein antigen which stimulates the immune system in the body to induce antibody reaction is generally restricted to a specific region corresponding to a size of 20 amino acids or less in the entire protein structure. Further, features of the epitope region are known to be similar even in different individuals such as humans, mice, goats, etc. Based on these facts, it was expected that the autoantibody-reactive epitope obtained from a liver cancer model mouse shows the same actions in the human body, and His-XC90p2-SA recombinant protein, of which XC90 antibody reaction specificity was confirmed, was applied to the detection of human autoantibody, and as a result, it was confirmed that the His-XC90p2-SA recombinant protein is able to detect autoantibodies in the human serum. The detailed method is as follows:

A biotin-coated ELISA plate (Thermo) was blocked with 300 µl per well of a blocking buffer (protein-free blocking buffer (Thermo), 5% bovine serum albumin) at 4° C. for 16 hours, and 200 ng per well of the recombinant streptavidin protein diluted with 100 µl of the blocking solution was added to coat the plate at 37° C. for 1 hour. After coating, the remaining recombinant protein was removed from the plate, which was then washed with TEST twice. After washing, 100 µl of the blocking buffer containing 1% gelatin was added to the plate, which was then treated with serum of a liver cancer patient or a normal person diluted with 100 µl of the blocking buffer at 1:100. Primary antibody reaction was performed at 37° C. for 2 hours, and antibodies remaining after reaction were washed with TEST six times. As a secondary antibody, 100 µl of anti-human IgGAM-HRP (Pierce) diluted with the protein-free blocking solution at 1:2500 was treated to the plate, and allowed to react at 37° C. for 90 minutes. After reaction, the plate was washed with TEST six times, and 100 µl of TMB solution was added to be reacted with HRP, and then absorbance at 450 nm was measured. ELISA of the human serum with the recombinant protein was repeated three times or more to confirm reproducibility. Of them, the most representative result is shown in FIG. 7A. Further, the result was analyzed by a receiver operating characteristic (ROC) curve. Cut off values which are diagnostic criteria for a diagnostic test are generally determined in a range where the area under the ROC curve is maximized. As a result, as shown in FIG. 7B, the serum of the normal person was discriminated from the serum of the liver cancer patient with 73.81% of sensitivity and 76.74% of specificity at a cut-off value of 1.067 maximizing the AUC area in the ELISA result of His-XC90p2-SA. These results suggest that ELISA of human serum by using the His-XC90p2-SA recombinant protein which is the epitope mimetic corresponding to XC90 antibody of the present invention may be usefully applied to the diagnostic test of liver cancer.

Example 10: Analysis of Complementarity Determining Regions (CDRs) of XC90 Antibody and Purification of Antibody After confirming that the XC90 antibody specifically recognizes the antigens expressed in cancer cells, the sequences of the complementarity determining regions (CDRs) of the XC90 antibody were analyzed to obtain information about the antibody-recognizing specificity of the corresponding antibody. $10^6$ XC90 antibody-producing cells were collected, and cDNA was synthesized from 5 µg of total RNA by an RNA kit (Invitrogen), and 1 µg of the synthesized cDNA, mouse heavy chain constant region primers (SEQ ID NOS: 18 and 19), and mouse light chain constant region primers (SEQ ID NOS: 20 and 21) were used to perform PCR, thereby amplifying the CDR containing regions of the mouse heavy and light chains (Table 3).

TABLE 3

Primers used for amplification of CDRs of heavy and light chains of autoantibody

| Type | Primer (5'-3') |
| --- | --- |
| Mouse heavy chain region | F: CTT CCG GAA TTC SAR GTN MAG CTG SAG SAG TCW GG (SEQ ID NO: 18)<br>R: GGA AGA TCT GAC ATT TGG GAA GGA CTG ACT CTC (SEQ ID NO: 19) |

TABLE 3-continued

Primers used for amplification of CDRs of heavy and light chains of autoantibody

| Type | Primer (5'-3') |
|---|---|
| Mouse light chain region | F: GGG AGC TCG AYAT TGT GMT SAC MCA RWC TMC A (SEQ ID NO: 20)<br>R: GGT GCA TGC GGA TAC AGT TGG TGC AGC ATC (SEQ ID NO: 21) |

The amplified regions were ligated to a pTOP Blunt V2 vector by using a TOPcloner Blunt kit (Enzynomics). The recombinant plasmids were transformed into *E. coli* DH5α, and plasmids were extracted from the transformed *E. coli*, followed by sequencing analysis. Protein sequences were determined from the analyzed nucleotide sequences, and analyzed based on Kabat CDR definition. As shown in FIG. 8, the heavy chain of the XC90 antibody was determined. As shown in FIG. 9, the light chain of the XC90 antibody was determined.

Through Examples, various autoantibody-producing clones were confirmed. Among the clones, particularly, the XC90 clone-derived antibody was characterized in the present invention, and it was confirmed that detection of the clone is possible in the sera of cancer patients, thereby being suggested as a tumor-associated autoantibody marker.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

Effect of the Invention

When anti-EIF3A autoantibody of the present invention is used as a diagnostic marker for liver cancer, the incidence of liver cancer may be diagnosed with 76.74% specificity and 73.81% sensitivity only by using non-invasive biological samples such as blood, plasma, serum, and lymphatic fluid without using an invasive tissue sample. Furthermore, a sequence of a peptide reacting with the marker is identified in the present invention. Therefore, it is not necessary to design a complex reacting substance for marker identification, and liver cancer may be easily diagnosed by using only the identified amino acid sequence, leading to the effective development of diagnostic products such as a diagnostic kit for liver cancer.

What is claimed is:

1. An autoantibody which specifically binds to EIF3A (Eukaryotic translation initiation factor 3 subunit A) protein or a fragment of EIF3A protein comprising a binding site to which the autoantibody binds,
   wherein the autoantibody comprises a heavy chain variable region comprising a heavy chain CDR1, the amino acid sequence of which is set forth in SEQ ID NO: 24; a heavy chain CDR2, the amino acid sequence of which is set forth in SEQ ID NO: 25; and a heavy chain CDR3, the amino acid sequence of which is set forth in SEQ ID NO: 26; and a light chain variable region comprising a light chain CDR1, the amino acid sequence of which is set forth in SEQ ID NO: 27; a light chain CDR2, the amino acid sequence of which is set forth in SEQ ID NO: 28; and a light chain CDR3, the amino acid sequence of which is set forth in SEQ ID NO: 29.

2. The autoantibody of claim 1, wherein the autoantibody binds to a peptide, the amino acid sequence of which the peptide is selected from the group consisting of the sequences set forth in SEQ ID NOs: 1 to 9.

3. The autoantibody of claim 1, wherein the autoantibody is produced by a hybridoma cell line deposited under Accession NO. KCTC 12590BP.

4. A hybridoma cell line producing the autoantibody which specifically binds to EIF3A protein of claim 1.

5. The hybridoma cell line of claim 4, wherein the hybridoma cell line is deposited under Accession NO. KCTC 12590BP.

6. A polypeptide comprising:
   (i) an amino acid sequence selected from the group consisting of the sequences set forth in SEQ ID NOS: 1 to 9, and
   (ii) additional cysteines at both ends of the amino acid sequence,
   wherein the polypeptide specifically binds to the autoantibody of claim 1.

7. A composition for diagnosing liver cancer, comprising an agent useful for measuring an expression level of the autoantibody which specifically binds to EIF3A protein or the fragment of EIF3A of claim 1, wherein the agent useful for measuring the expression level of the autoantibody is a polypeptide comprising an antigenic determinant peptide sequence, the amino acid sequence of which the polypeptide is selected from the group of sequences consisting of SEQ ID NOS: 1 to 9.

8. A kit for diagnosing liver cancer, comprising the composition of claim 7.

9. The kit of claim 8, wherein the kit is useful for performing a method selected from the group consisting of Western blotting, ELISA (Enzyme Linked Immunosorbent Assay), radioimmunoassay, radioimmunodiffusion, Ouchterlony immunodiffusion, rocket immunoelectrophoresis, immunohistostaining, immunoprecipitation assay, complement fixation assay, FACS, protein chip assay, and combinations thereof.

10. A composition for diagnosing liver cancer, comprising a polypeptide useful for measuring an expression level of the autoantibody of claim 1, wherein the polypeptide has a sequence which comprises:
   (i) an amino acid sequence selected from the group consisting of SEQ ID NOs: 1 to 9, and
   (ii) additional cysteines at both ends of the amino acid sequence, and
   wherein the polypeptide specifically binds to said autoantibody.

11. A kit for diagnosing liver cancer, comprising the composition of claim 10.

* * * * *

SEQUENCE LISTING

```
<160> NUMBER OF SEQ ID NOS: 31

<210> SEQ ID NO 1
<211> LENGTH: 7
<212> TYPE: PRT
<213> ORGANISM: Artificial Sequence
<220> FEATURE:
<223> OTHER INFORMATION: XC90p1 epitope

<400> SEQUENCE: 1

Phe Pro Phe Pro Ser Ser Leu
1               5

<210> SEQ ID NO 2
<211> LENGTH: 7
<212> TYPE: PRT
<213> ORGANISM: Artificial Sequence
<220> FEATURE:
<223> OTHER INFORMATION: XC90p2 epitope

<400> SEQUENCE: 2

Pro Val Arg Ser Gly Phe Pro
1               5

<210> SEQ ID NO 3
<211> LENGTH: 7
<212> TYPE: PRT
<213> ORGANISM: Artificial Sequence
<220> FEATURE:
<223> OTHER INFORMATION: XC90p3 epitope
```

```
<400> SEQUENCE: 3

Leu Pro Trp Pro Ser Ser Leu
1               5

<210> SEQ ID NO 4
<211> LENGTH: 7
<212> TYPE: PRT
<213> ORGANISM: Artificial Sequence
<220> FEATURE:
<223> OTHER INFORMATION: XC90p4 epitope

<400> SEQUENCE: 4

Pro Ser Arg His Ser Gly Trp
1               5

<210> SEQ ID NO 5
<211> LENGTH: 7
<212> TYPE: PRT
<213> ORGANISM: Artificial Sequence
<220> FEATURE:
<223> OTHER INFORMATION: XC90p5 epitope

<400> SEQUENCE: 5

Pro Ser Arg His Ser Gly Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: XC90p6 epitope

<400> SEQUENCE: 6

Pro Ala Arg His Ser Gly Phe
1               5

<210> SEQ ID NO 7
<211> LENGTH: 7
<212> TYPE: PRT
<213> ORGANISM: Artificial Sequence
<220> FEATURE:
<223> OTHER INFORMATION: XC90p7 epitope

<400> SEQUENCE: 7

Pro Ala Arg Thr Ser Trp Pro
1               5

<210> SEQ ID NO 8
<211> LENGTH: 7
<212> TYPE: PRT
<213> ORGANISM: Artificial Sequence
<220> FEATURE:
<223> OTHER INFORMATION: XC90p8 epitope

<400> SEQUENCE: 8

Pro Pro Arg Thr Gly Phe Gln
1               5

<210> SEQ ID NO 9
<211> LENGTH: 7
<212> TYPE: PRT
<213> ORGANISM: Artificial Sequence
<220> FEATURE:
<223> OTHER INFORMATION: XC90p9 epitope

<400> SEQUENCE: 9
```

Pro Ala Arg Ser Gly Tyr Pro
1               5

<210> SEQ ID NO 10
<211> LENGTH: 42
<212> TYPE: DNA
<213> ORGANISM: Artificial Sequence
<220> FEATURE:
<223> OTHER INFORMATION: F-primer for streptavidin

<400> SEQUENCE: 10
gcggccgcag gttcgggttc ggccgacccc tccaaggact cg            42

<210> SEQ ID NO 11
<211> LENGTH: 30
<212> TYPE: DNA
<213> ORGANISM: Artificial Sequence
<220> FEATURE:
<223> OTHER INFORMATION: R-primer for streptavidin

<400> SEQUENCE: 11
ctcgagtcat cactgctgaa cggcgtcgag                          30

<210> SEQ ID NO 12
<211> LENGTH: 54
<212> TYPE: DNA
<213> ORGANISM: Artificial Sequence
<220> FEATURE:
<223> OTHER INFORMATION: F-primer for XC90p2 epitope

<400> SEQUENCE: 12
tatgggtggt gcgtgcccgg ttcgttctgg tttcccgtgc ggtggaggtt cggc    54

<210> SEQ ID NO 13
<211> LENGTH: 56
<212> TYPE: DNA
<213> ORGANISM: Artificial Sequence
<220> FEATURE:
<223> OTHER INFORMATION: R-primer for XC90p2 epitope

<400> SEQUENCE: 13
ggccgccgaa cctccaccgc acgggaaacc agaacgaacc gggcacgcac caccca    56

<210> SEQ ID NO 14
<211> LENGTH: 30
<212> TYPE: DNA
<213> ORGANISM: Artificial Sequence
<220> FEATURE:
<223> OTHER INFORMATION: F-primer for Eph-STA

<400> SEQUENCE: 14
catatgggtg gtgcggccgc aggttcgggt                          30

<210> SEQ ID NO 15
<211> LENGTH: 30
<212> TYPE: DNA
<213> ORGANISM: Artificial Sequence
<220> FEATURE:
<223> OTHER INFORMATION: R-primer for Eph-STA

<400> SEQUENCE: 15
ctcgagtcat cactgctgaa cggcgtcgag                          30

<210> SEQ ID NO 16
<211> LENGTH: 54

```
<212> TYPE: DNA
<213> ORGANISM: Artificial Sequence
<220> FEATURE:
<223> OTHER INFORMATION: F-primer for DsbA

<400> SEQUENCE: 16
ctcgagcacc accaccacca ccactgatga attattgaag cttatgaaga attt        54

<210> SEQ ID NO 17
<211> LENGTH: 32
<212> TYPE: DNA
<213> ORGANISM: Artificial Sequence
<220> FEATURE:
<223> OTHER INFORMATION: R-primer for DsbA

<400> SEQUENCE: 17
ctcgagttat tatttttct cggacagata tt                                 32

<210> SEQ ID NO 18
<211> LENGTH: 35
<212> TYPE: DNA
<213> ORGANISM: Artificial Sequence
<220> FEATURE:
<223> OTHER INFORMATION: F-primer for heavy chain constant region
<220> FEATURE:
<221> NAME/KEY: misc_feature
<222> LOCATION: (18)..(18)
<223> OTHER INFORMATION: Any Nucleotide

<400> SEQUENCE: 18
cttccggaat tcsargtnma gctgsagsag tcwgg                             35

<210> SEQ ID NO 19
<211> LENGTH: 33
<212> TYPE: DNA
<213> ORGANISM: Artificial Sequence
<220> FEATURE:
<223> OTHER INFORMATION: R-primer for heavy chain constant region

<400> SEQUENCE: 19
ggaagatctg acatttggga aggactgact ctc                               33

<210> SEQ ID NO 20
<211> LENGTH: 32
<212> TYPE: DNA
<213> ORGANISM: Artificial Sequence
<220> FEATURE:
<223> OTHER INFORMATION: F-primer for light chain constant region

<400> SEQUENCE: 20
gggagctcga yattgtgmts acmcarwctm ca                                32

<210> SEQ ID NO 21
<211> LENGTH: 30
<212> TYPE: DNA
<213> ORGANISM: Artificial Sequence
<220> FEATURE:
<223> OTHER INFORMATION: R-primer for light chain constant region

<400> SEQUENCE: 21
ggtgcatgcg gatacagttg gtgcagcatc                                   30

<210> SEQ ID NO 22
<211> LENGTH: 125
<212> TYPE: PRT
<213> ORGANISM: Artificial Sequence
<220> FEATURE:
```

```
<223> OTHER INFORMATION: variable region of heavy chain
<220> FEATURE:
<221> NAME/KEY: MISC_FEATURE
<222> LOCATION: (1)..(1)
<223> OTHER INFORMATION: Either Glutamine or Glutamic Acid
<220> FEATURE:
<221> NAME/KEY: MISC_FEATURE
<222> LOCATION: (5)..(5)
<223> OTHER INFORMATION: Either Glutamine or Glutamic Acid

<400> SEQUENCE: 22

Xaa Val Lys Leu Xaa Glu Ser Gly Ala Glu Leu Val Met Pro Gly Ala
 1               5                  10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asp Pro Ser Asp Ser Tyr Thr Asn Tyr Asn Gln Lys Phe
    50                  55                  60

Lys Gly Lys Ser Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Lys Gly Ser Tyr Ala Pro Phe Ala Tyr Trp Gly Gln Gly Thr Leu
            100                 105                 110

Val Thr Val Ser Ala Glu Ser Gln Ser Phe Pro Asn Val
        115                 120                 125

<210> SEQ ID NO 23
<211> LENGTH: 115
<212> TYPE: PRT
<213> ORGANISM: Artificial Sequence
<220> FEATURE:
<223> OTHER INFORMATION: variable region of light chain
<220> FEATURE:
<221> NAME/KEY: MISC_FEATURE
<222> LOCATION: (7)..(7)
<223> OTHER INFORMATION: Either Threonine or Serine
<220> FEATURE:
<221> NAME/KEY: MISC_FEATURE
<222> LOCATION: (8)..(8)
<223> OTHER INFORMATION: Either Threonine or Proline

<400> SEQUENCE: 23

Asp Ile Val Ile Thr Gln Xaa Xaa Ala Ile Met Ser Ala Ser Pro Gly
 1               5                  10                  15

Glu Lys Val Thr Ile Ser Cys Ser Ala Ser Ser Val Ser Tyr Met
            20                  25                  30

Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Pro Thr
                85                  90                  95

Phe Gly Gly Gly Thr Lys Leu Glu Ile Lys Arg Ala Asp Ala Ala Pro
            100                 105                 110

Thr Val Ser
        115
```

```
<210> SEQ ID NO 24
<211> LENGTH: 10
<212> TYPE: PRT
<213> ORGANISM: Artificial Sequence
<220> FEATURE:
<223> OTHER INFORMATION: CDR1 of heavy chain

<400> SEQUENCE: 24

Gly Tyr Thr Phe Thr Ser Tyr Trp Ile His
1               5                   10

<210> SEQ ID NO 25
<211> LENGTH: 17
<212> TYPE: PRT
<213> ORGANISM: Artificial Sequence
<220> FEATURE:
<223> OTHER INFORMATION: CDR2 of heavy chain

<400> SEQUENCE: 25

Glu Ile Asp Pro Ser Asp Ser Tyr Thr Asn Tyr Asn Gln Lys Phe Lys
1               5                   10                  15

Gly

<210> SEQ ID NO 26
<211> LENGTH: 8
<212> TYPE: PRT
<213> ORGANISM: Artificial Sequence
<220> FEATURE:
<223> OTHER INFORMATION: CDR3 of heavy chain

<400> SEQUENCE: 26

Gly Ser Tyr Ala Pro Phe Ala Tyr
1               5

<210> SEQ ID NO 27
<211> LENGTH: 10
<212> TYPE: PRT
<213> ORGANISM: Artificial Sequence
<220> FEATURE:
<223> OTHER INFORMATION: CDR1 of light chain

<400> SEQUENCE: 27

Ser Ala Ser Ser Ser Val Ser Tyr Met Tyr
1               5                   10

<210> SEQ ID NO 28
<211> LENGTH: 7
<212> TYPE: PRT
<213> ORGANISM: Artificial Sequence
<220> FEATURE:
<223> OTHER INFORMATION: CDR2 of light chain

<400> SEQUENCE: 28

Arg Thr Ser Asn Leu Ala Ser
1               5

<210> SEQ ID NO 29
<211> LENGTH: 9
<212> TYPE: PRT
<213> ORGANISM: Artificial Sequence
<220> FEATURE:
<223> OTHER INFORMATION: CDR3 of light chain

<400> SEQUENCE: 29

Gln Gln Tyr His Ser Tyr Pro Pro Thr
1               5
```

```
<210> SEQ ID NO 30
<211> LENGTH: 375
<212> TYPE: DNA
<213> ORGANISM: Artificial Sequence
<220> FEATURE:
<223> OTHER INFORMATION: variable region of heavy chain

<400> SEQUENCE: 30
sargtmaagc tgsaggagtc tggggctgag cttgtgatgc ctggggcttc agtgaagctg      60
tcctgcaagg cttctggcta caccttcacc agctactgga tacactgggt gaaacagagg     120
cctggacaag gccttgagtg gatcggagag attgatcctt ctgatagtta tactaactac     180
aatcaaaagt tcaagggcaa gtccacattg actgtagaca atcctccaa cacagcctac      240 atgcagctca gcagcctgac atctgaggac tctgcggtct attactgtgc aaaaggctct     300
tatgcccctt ttgcttactg gggccaaggg actctggtca ctgtctctgc agagagtcag     360
tccttcccaa atgtc                                                      375

<210> SEQ ID NO 31
<211> LENGTH: 345
<212> TYPE: DNA
<213> ORGANISM: Artificial Sequence
<220> FEATURE:
<223> OTHER INFORMATION: variable region of light chain

<400> SEQUENCE: 31
gayattgtga tcacccarwc tmcagcaatc atgtctgcat ctccagggga gaaggtcacc      60
atatcctgca gtgccagctc aagtgtaagt tacatgtact ggtaccagca gaagccagga     120
tcctccccca aaccctggat ttatcgcaca tccaacctgg cttctggagt ccctgctcgc     180
ttcagtggca gtgggtctgg gacctcttac tctctcacaa tcagcagcat ggaggctgaa     240
gatgctgcca cttattactg ccagcagtat catagttacc caccgacgtt cggtggaggc     300
accaagctgg aaatcaaacg ggctgatgct gcaccaactg tatcc                     345
```